US010258683B2

(12) United States Patent
Bailey et al.

(10) Patent No.: US 10,258,683 B2
(45) Date of Patent: Apr. 16, 2019

(54) ENGINEERED VESICLES COMPRISING ANTIGENIC PEPTIDES AND THE USES THEREOF AS MODULATORS OF IMMUNE RESPONSES

(71) Applicant: George Mason University, Fairfax, VA (US)

(72) Inventors: Charles Bailey, Manassas, VA (US); Aarthi Narayanan, Manassas, VA (US)

(73) Assignee: GEORGE MASON UNIVERSITY, Fairfax, VA (US)

( * ) Notice: Subject to any disclaimer, the term of this patent is extended or adjusted under 35 U.S.C. 154(b) by 76 days.

(21) Appl. No.: 15/167,239

(22) Filed: May 27, 2016

(65) Prior Publication Data

US 2016/0375121 A1     Dec. 29, 2016

Related U.S. Application Data

(60) Provisional application No. 62/166,967, filed on May 27, 2015.

(51) Int. Cl.
*A61K 39/12* (2006.01)
*C07K 14/005* (2006.01)
*A61K 39/00* (2006.01)

(52) U.S. Cl.
CPC ............ *A61K 39/12* (2013.01); *C07K 14/005* (2013.01); *A61K 2039/5256* (2013.01); *A61K 2039/552* (2013.01); *C12N 2770/36122* (2013.01); *C12N 2770/36134* (2013.01); *C12N 2770/36151* (2013.01); *C12N 2770/36171* (2013.01)

(58) Field of Classification Search
None
See application file for complete search history.

(56) References Cited

PUBLICATIONS

Daleke-Schermerhorn et al. Decoration of Outer Membrane Vesicles with Multiple Antigens by Using an Autotransporter Approach. AEM. 2014; 80(18): 5854-5865.*

(Continued)

*Primary Examiner* — Janet L Andres
*Assistant Examiner* — Stuart W Snyder
(74) *Attorney, Agent, or Firm* — Ballard Spahr LLP

(57) ABSTRACT

Disclosed herein are single nucleic acid constructs comprising a vector, wherein the vector comprises: a first nucleic acid sequence, wherein the first nucleic acid sequence comprises one or more antigenic sequences of interest, one or more spacer sequences and one or more hydrophobic anchor sequences, operably linked to a first transcriptional control element; a second nucleic acid sequence, wherein the second nucleic acid sequence comprises one or more pathogen-associated molecular pattern (PAMP) sequences operably linked to a second transcriptional control element; a third nucleic acid sequence, wherein the third nucleic acid sequence comprises one or more cell surface receptor binding sequences operably linked to a third transcriptional control element; and a selectable marker. Also described herein, are methods of making the single nucleic acid constructs and methods of administering the single nucleic acid constructs for the treatment or prevention of infections and cancer. Also described herein are cell lines and engineered vesicles made using the single nucleic acid constructs described herein.

18 Claims, 11 Drawing Sheets

(56) References Cited

PUBLICATIONS

Qin JY, Zhang L, Clift KL, Hulur I, Xiang AP, et al. (2010) Systematic Comparison of Constitutive Promoters and the Doxycycline-Inducible Promoter. PLoS ONE 5(5): e10611. doi:10.1371/journal.pone.0010611.*

Sedlik et al. Different immunogenicity but similar antitumor efficacy of two DNA vaccines coding for an antigen secreted in different membrane vesicle-associated formsJ. Extracellular Vesicles. 2014, 3: 24646—http://dx.doi.org/10.3402/jev.v3.24646.*

Glickman and Adir, The Proteasome and the Delicate Balance between Destruction and Rescue. PLoS Biol. 2004; 2(1): 0025-0027.*

Daleke-Schermerhorn et al. Decoration of Outer Membrane Vesicles with Multiple Antigens by Using an Autotransporter Approach. Appl. Environ. Microbiol. 2014; 80(18): 5854-5865.*

Miyauchi et al. Simultaneous expression of the bacterial Dictyoglomus thermophilum xynB gene under three different Trichoderma reesei promoters. New Biotech. 2014; 31(1): 98-103.*

Qin et al. Systematic Comparison of Constitutive Promoters and the Doxycycline-Inducible Promoter. PLoS ONE 5(5): e10611.*

Girl, P.K. et al., Proteomic analysis identifies highly antigenic proteins in exosomes from *M. tuberculosis*-infected and culture filtrate protein-treated macrophages. Proteomics. 2010; 10(17):3190-202.

Liu, M.L. et al., Cholesterol-induced membrane microvesicles as novel carriers of damage-associated molecular patterns: mechanisms of formation, action, and detoxification. Arterioscler Thromb Vasc Biol. 2012; 32(9):2113-21.

Meckes, D.G. Jr., and Raab-Traub, N., Microvesicles and viral infection. J Virol. 2011; (24):12844-54.

Morel, O. et al., Cellular microparticles: a disseminated storage pool of bioactive vascular effectors. Curr Opin Hematol. 2004; 11(3):156-64.

Pegtel, D.M. et al., Functional delivery of viral miRNAs via exosomes. Proc Natl Acad Sci U S A 2010; 107(14):6328-33.

Pegtel, D.M. et al., Viral miRNAs exploiting the endosomal-exosomal pathway for intercellular cross-talk and immune evasion. Biochim Biophys Acta. 2011; 1809(11-12):715-21.

Singh, P.P. et al., Exosomes released from M. tuberculosis infected cells can suppress IFN-γ mediated activation of naïve macrophages. PLoS One. 2011; 6(4):e18564 (10 pages).

* cited by examiner

FIG. 1

A) Specific target plasmids that encode individual viral proteins are utilized
B) Plasmids are quality checked and transfected into receptive cells
C) Supernatants are harvested at multiple time points
D) EVs are enriched by high speed centrifugation approaches

FIG. 11 understand# ENGINEERED VESICLES COMPRISING ANTIGENIC PEPTIDES AND THE USES THEREOF AS MODULATORS OF IMMUNE RESPONSES

CROSS REFERENCE TO RELATED APPLICATIONS

This application claims the benefit of the filing date of U.S. Provisional Application No. 62/166,967, which was filed on May 27, 2015. The content of this earlier filed application is hereby incorporated by reference in its entirety.

SUMMARY

Disclosed herein are single nucleic acid constructs comprising a vector, wherein the vector comprises: a first nucleic acid sequence, wherein the first nucleic acid sequence comprises one or more antigenic sequences of interest, one or more spacer sequences and one or more hydrophobic anchor sequences, operably linked to a first transcriptional control element; a second nucleic acid sequence, wherein the second nucleic acid sequence comprises one or more pathogen-associated molecular pattern (PAMP) sequences operably linked to a second transcriptional control element; a third nucleic acid sequence, wherein the third nucleic acid sequence comprises one or more cell surface receptor binding sequences operably linked to a third transcriptional control element; and a selectable marker.

Disclosed herein are cells that produce extracellular vesicles, wherein the extracellular vesicles comprise one or more antigenic peptides, one or more hydrophobic anchor peptides; one or more PAMPs; and one or more cell surface receptor binding peptides.

Disclosed herein are methods of preventing or treating an infection or a disease, the method comprising: (a) identifying a subject in need of prevention or treatment of an infection or disease; and (b) administering a composition comprising: (i) a first nucleic acid sequence, wherein the first nucleic acid sequence comprises one or more antigenic sequences of interest, one or more spacer sequences and one or more hydrophobic anchor sequences, operably linked to a first transcriptional control element; (ii) a second nucleic acid sequence, wherein the second nucleic acid sequence comprises one or more pathogen-associated molecular pattern (PAMP) sequences operably linked to a second transcriptional control element; and (iii) a third nucleic acid sequence, wherein the third nucleic acid sequence comprises one or more cell surface receptor binding sequences operably linked to a third transcriptional control element.

Disclosed herein are methods of making extracellular vesicles, the methods comprising: (a) introducing a first nucleic acid sequence, wherein the first nucleic acid sequence comprises one or more antigenic sequences of interest, one or more spacer sequences and one or more hydrophobic anchor sequences, operably linked to a first transcriptional control element; (b) a second nucleic acid sequence, wherein the second nucleic acid sequence comprises one or more pathogen-associated molecular pattern sequences operably linked to a second transcriptional control element; (c) a third nucleic acid sequence, wherein the third nucleic acid sequence comprises one or more cell surface receptor binding sequences operably linked to a third transcriptional control element; (d) a selectable marker; and (e) maintaining the cell under conditions that allow expression of (a), (b), (c) and (d) of the extracellular vesicle; wherein the one or more antigenic sequences of interest is a nucleic acid sequence encoding one or more peptides derived from a virus, a toxin, a bacterium or an allergen. In some aspects, (a)-(d) are introduced together in one or more of the single nucleic acid constructs described herein.

Disclosed herein are engineered extracellular vesicles comprising one or more antigenic peptides, one or more hydrophobic anchor peptides; one or more PAMPs; and one or more cell surface receptor binding peptides.

Disclosed herein are engineered extracellular vesicles comprising one or more antigenic proteins, one or more hydrophobic anchor proteins; one or more PAMPs; and one or more cell surface receptor binding proteins.

Disclosed herein are engineered vesicles that contain a viral peptide. For example, disclosed herein are engineered vesicles comprising one or more antigenic sequences of interest. The antigenic sequences of interest can be virus-derived, bacteria-derived, or other pathogen-derived, such as parasite-derived components, toxin-derived or allergen-derived peptide components. In an aspect, the antigenic sequences of interest can function to modulate innate immune responses in receptive hosts. The engineered vesicles can be used as elicitors and modulators of immune responsiveness. The vesicles disclosed herein can be produced by human or other types of cells and are referred to herein as extracellular vesicles (EVs).

Disclosed herein are methods to develop a vaccine or an immune modulatory platform that can be utilized singly or in combination with other candidates relevant to the viral or bacterial infectious agent to confer protection to the host. For example, the delivery platform described herein can be used singly or in combination with other candidates as an immune-modulatory agent to confer immunoprotective responses to a host.

Disclosed herein are methods to introduce to a host, an engineered vesicle that can be used to help a host to mount an effective immune response to, for instance, an infectious agent (e.g., viral or bacterial infectious agent).

Disclosed herein are methods wherein a target candidate (e.g., EV) or platform or technology can be merged with one or more of the existing delivery mechanisms (e.g., injections) while also being amenable to other methodologies (e.g., aerosols, topicals).

Disclosed herein are compositions and methods that can protect target analytes (for example, by encasing target analytes (e.g., viral peptides) from rapid degradation when introduced into the appropriate host due to host based enzymes.

Disclosed herein are delivery platforms capable of facilitating membrane fusion with target host cells to enhance the probability of antigenic sequence (e.g., viral peptides) delivery.

Disclosed herein are delivery platforms wherein an analyte (e.g., viral peptides) can elicit an immune response based on modifications of and/or interactions with the host innate immune and adaptive immune responses.

Disclosed herein are methods for making or engineering vesicles from different cell types and/or different organisms to produce an organism specific delivery system. In an aspect, the cells can be the subject's own cells, tumor cells, cancer cells, or umbilical cord-derived stem cells. Cells suitable for the methods for making or engineering vesicles include, but are not limited to, vertebrate cells, such as a mammal, a fish, a bird, a reptile, or an amphibian. In some aspects the cells methods for making or engineering vesicles are human cells. In some aspects the cells methods for making or engineering vesicles are tumor cells, cancer cells, or umbilical cord-derived stem cells In an aspect, the delivery system can be used to deliver antigenic peptides to non-human hosts (e.g., pets, livestock). In another aspect, the delivery system disclosed herein can be used in nontraditional antigen delivery methods including, for example, inhalation, ingestion or dermal applications.

BRIEF DESCRIPTION OF THE DRAWINGS

Figure 1:
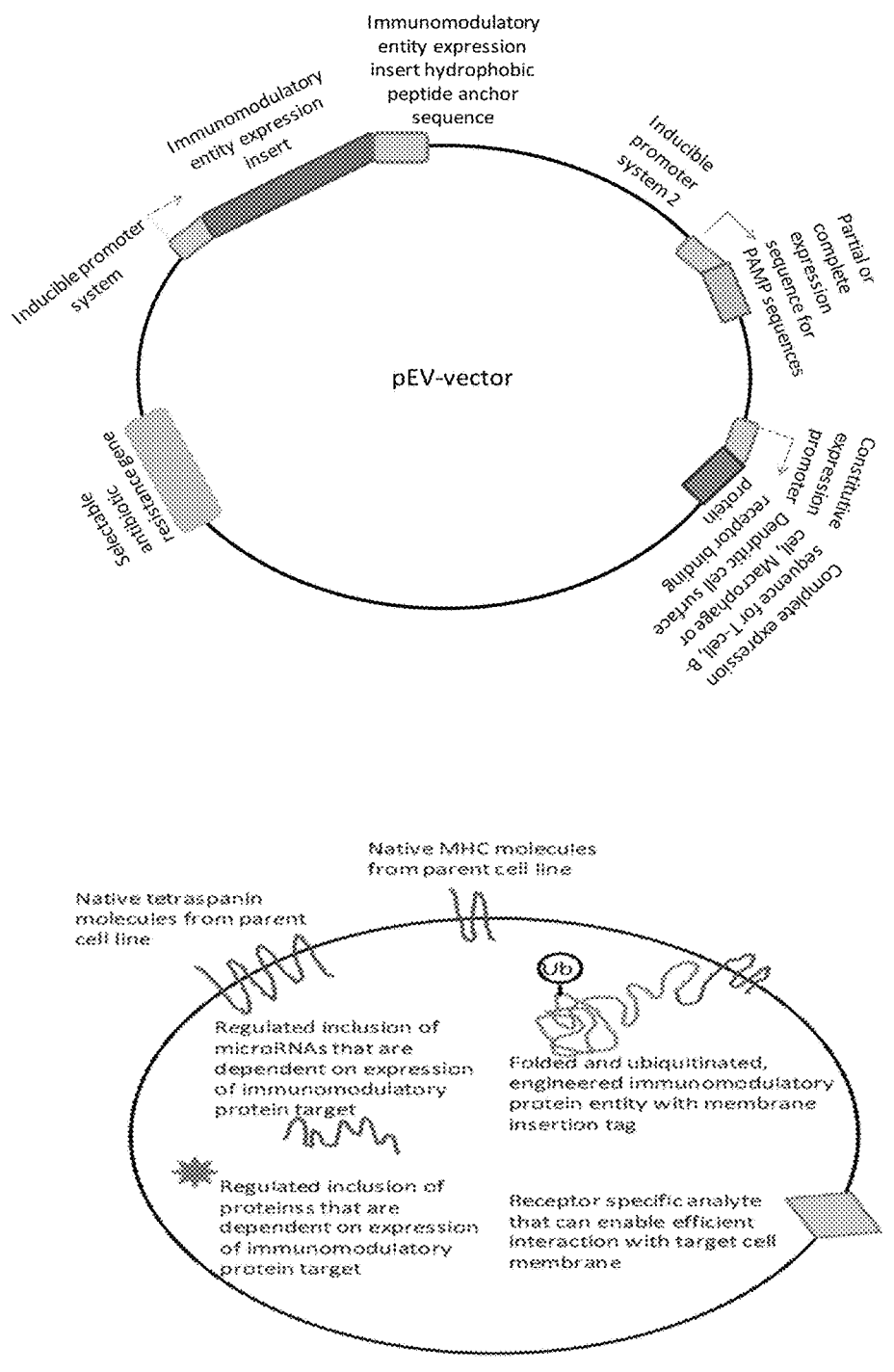

FIG. 1 is a schematic showing the structure of a plasmid vector designated pEV-vector (top) and various components common to extracellular vesicles described herein (bottom).

FIG. 4A shows 293T cells that were transfected with a plasmid construct that expressed the viral glycoprotein (red) as colocalizing with CD63 (green), a surface marker that is included in EVs (colocalization indicated by yellow). FIG. 4B shows a single cell where the viral glycoprotein colocalized with CD63 (yellow).

Figure 5:
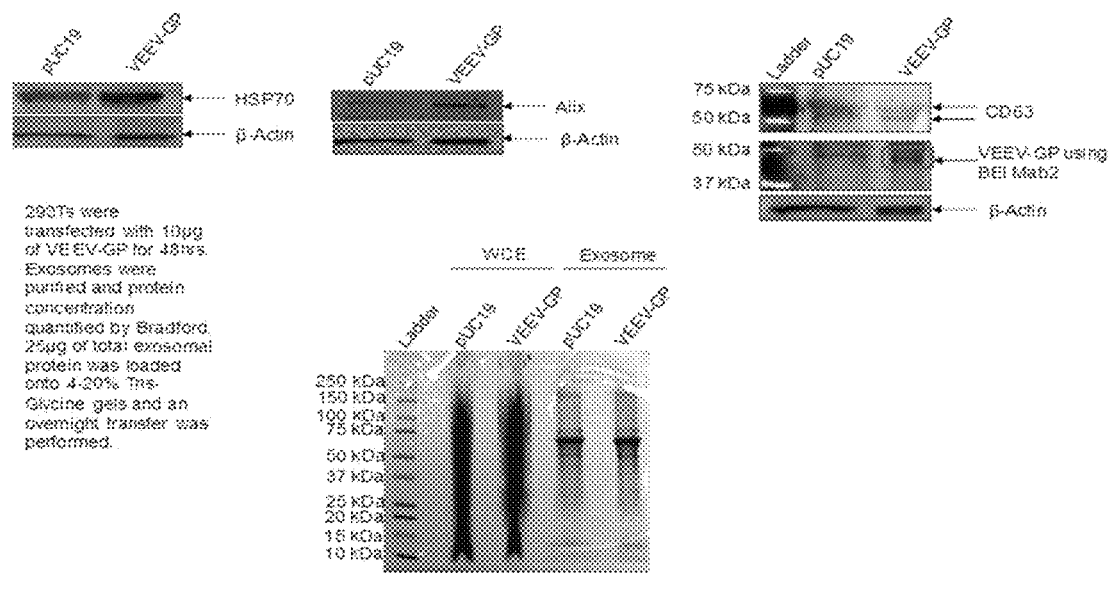

FIG. 5 shows exosome characterization from Venezuelan Equine Encephalitis Virus (VEEV)-glycoprotein (GP) transfected 293T cells at 48 hours post transfection.

FIG. 6A shows EVs include viral glycoprotein. FIG. 6B shows the intracellular expression for validation purposes. FIG. 6C shows the quantification of relative levels of glycoprotein EV when compared to intracellular pools (based on normalization to actin, the glycoproteins are more favorably included in the EVs). FIG. 6D shows the relative quantification of background noise relevant to the glycoprotein signal in intracellular and EV fractions.

FIG. 7 shows the antigenic sequences of interest that is enclosed in the extracellular vesicles (EVs) are protected from degradation.

FIGS. 8A-B show the detection of the foreign protein entity in different types of cells. FIG. 8A shows uptake of Venezuelan Equine Encephalitis Virus (VEEV) glycoprotein antigen in 293T cells that were overlaid with the glycoprotein containing EVs. FIG. 8B shows the uptake of VEEV glycoprotein in human macrophage cells that were overlaid with the glycoprotein containing extracellular vesicles (EVs).

FIG. 9 is a schematic illustrating the methods used to test if the engineered extracellular vesicle is capable of affording immunological survival to an animal in the face of a lethal exposure to an infectious agent.

FIG. 10A shows the schematic of immunization of the mice prior to challenge with the viral agent; the schematic also illustrates the duration between successive immunizations and the duration post challenge up to the point when the animals were sacrificed and the experiment terminated. FIG. 10B shows the survival curves of animals that were vaccinated with the antigen containing vesicles (EV, EV+boost) versus those that were vaccinated with a sham (PBS only).

FIG. 11 is a schematic illustration showing the process of engineering EVs as vaccine candidates.

DETAILED DESCRIPTION

Figure 2:
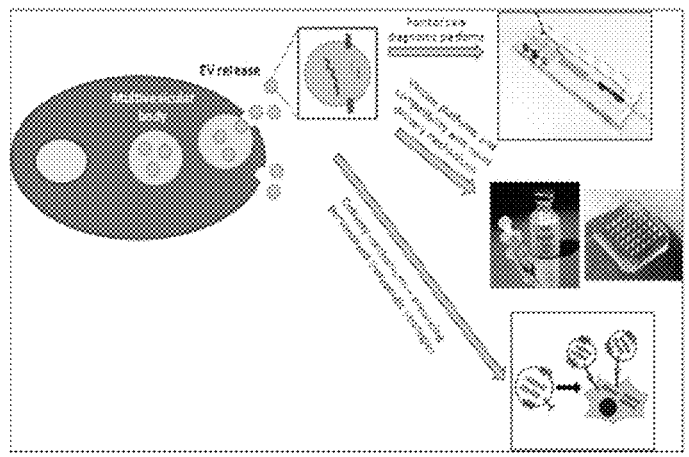
FIG. 2 illustrates the use of engineered extracellular vesicles (EVs) as engineered immunomodulatory entities.

The present disclosure can be understood more readily by reference to the following detailed description of the invention, the figures and the examples included herein.

Before the present methods and compositions are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for an infectious disease, such as, for example, prior to the administering step.

As used herein, the term "comprising" can include the aspects "consisting of" and "consisting essentially of."

As used in the specification and the appended claims, the singular forms "a," "an" and "the" can include plural referents unless the context clearly dictates otherwise. Thus, for example, reference to "a compound" includes mixtures of compounds; reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, an aspect includes from the one particular value and/or to the other particular value. Similarly, when values are expressed as approximations, by use of the antecedent "about," it will be understood that the particular value forms an aspect. It will be further understood that the endpoints of each of the ranges are significant both in relation to the other endpoint, and independently of the other endpoint.

The word "or" as used herein means any one member of a particular list and also includes any combination of members of that list.

"Inhibit," "inhibiting" and "inhibition" mean to diminish or decrease an activity, response, condition, disease, or other biological parameter. This can include, but is not limited to, the complete ablation of the activity, response, condition, or disease. This may also include, for example, a 10% inhibition or reduction in the activity, response, condition, or disease as compared to the native or control level. Thus, in an aspect, the inhibition or reduction can be a 10, 20, 30, 40, 50, 60, 70, 80, 90, 100%, or any amount of reduction in between as compared to native or control levels. In an aspect, the inhibition or reduction is 10-20, 20-30, 30-40, 40-50, 50-60, 60-70, 70-80, 80-90, or 90-100% as compared to native or control levels. In an aspect, the inhibition or reduction is 0-25, 25-50, 50-75, or 75-100% as compared to native or control levels.

"Modulate", "modulating" and "modulation" as used herein mean a change in activity or function or number. The change may be an increase or a decrease, an enhancement or an inhibition of the activity, function or number.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, in an aspect, the increase or promotion can be a 10, 20, 30, 40, 50, 60, 70, 80, 90, 100%, or more, or any amount of promotion in between compared to native or control levels. In an aspect, the increase or promotion is 10-20, 20-30, 30-40, 40-50, 50-60, 60-70, 70-80, 80-90, or 90-100% as compared to native or control levels. In an aspect, the increase or promotion is 0-25, 25-50, 50-75, or 75-100%, or more, such as 200, 300, 500, or 1000% more as compared to native or control levels. In an aspect, the increase or promotion can be greater than 100 percent as compared to native or control levels, such as 100, 150, 200, 250, 300, 350, 400, 450, 500% or more as compared to the native or control levels.

As used herein, the term "determining" can refer to measuring or ascertaining a quantity or an amount or a change in activity. For example, determining the amount of a disclosed polypeptide in a sample as used herein can refer to the steps that the skilled person would take to measure or ascertain some quantifiable value of the polypeptide in the sample. The art is familiar with the ways to measure an amount of the disclosed polypeptides and disclosed nucleotides in a sample.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the phrase "antigenic sequence" or "antigenic sequence of interest" refers to a nucleic acid sequence that is capable of encoding a peptide sequence that can illicit an immune response. For example, an antigenic sequence of interest can be a nucleic acid sequence that encodes a full or partial (e.g., a fragment) peptide sequence that is capable of eliciting an immune response. It can be partly or entirely heterologous (i.e., foreign to a cell into which it is introduced).

As used herein, the phrase "hydrophobic anchor sequence" refers to a nucleic acid sequence capable of encoding a peptide sequence that is composed of hydrophobic amino acid residues and is capable of inserting into the membrane of a cell or vesicle one or more times.

As used herein, the phrase "pathogen-associated molecular pattern sequences" refers to a nucleic acid sequence that is capable of encoding a peptide sequence that can be recognized by one or more cells considered to be part of the innate immune system.

As used herein, the phrase "cell surface binding sequences" refers to sequence capable of encoding a peptide that can bind to a surface receptor of an immune cell. Examples include, but are not limited to, immune cell surface receptor antigens such as T-cells, B-cells, macrophages or dendritic cell surface receptor binding peptides.

As used herein, the term "vector" or "construct" refers to a nucleic acid sequence capable of transporting into a cell another nucleic acid to which the vector sequence has been linked. The term "expression vector" includes any vector, (e.g., a plasmid, cosmid or phage chromosome) containing a gene construct in a form suitable for expression by a cell (e.g., linked to a transcriptional control element). The terms "plasmid" and "vector" can be used interchangeably, as a plasmid is a commonly used form of vector. Moreover, this disclosure is intended to include other vectors which serve equivalent functions.

The benefit to animal or poultry (e.g., chicken) to be treated is either statistically significant or at least perceptible the caretaker, handler, farmer, veterinarian, etc.

The present disclosure is not to be limited in scope by the specific embodiments described herein. Indeed, various modifications of the disclosure in addition to those described herein will become apparent to those skilled in the art from the foregoing description and the accompanying figures. Such modifications are intended to fall within the scope of the claims.

References, including patents, patent applications, and various publications are cited and discussed throughout the specification. The citation and/or discussion of such references is provided merely to clarify the description of the present invention and is not an admission that any such reference is "prior art" to the present invention. All references cited and discussed in this specification are each incorporated herein by reference in its entirety and to the same extent as if each reference was individually incorporated by reference.

Introduction

The composition and methods disclosed herein can be used to elicit and/or enhance immune responsiveness to, for example, vaccines, in a host. The vesicles disclosed herein can be produced by human cells and are referred to as extracellular vesicles (EVs). Vesicles can also be produced by cells derived from other hosts. For example, animal-derived cells can be used to enhance organism specific immune responsiveness.

The EVs disclosed herein can be engineered to comprise one or more foreign peptides (e.g., virus-derived peptides) or one or more antigenic sequences of interest. The EVs can be produced by transformed human cells by, for example, utilizing human-derived or other organism-derived primary and/or transformed cells, stem cells. EVs can be produced that are more amenable for utility in different organisms.

The engineered EVs described herein do not require an entire protein entity such as a full virus or a full toxin or all of the constituents of a venom, for example. Thus, in an aspect, the engineered EVs can be used to minimize, reduce or eliminate one or more undesirable side effects. In an aspect, the engineered EVs disclosed herein can lead to or be associated with a low reactogenic effect. For instance, engineered EVs that are low in reactogenic effects may be useful in immunocompromised subjects, older populations and young populations (e.g., infants).

EVs are lipid bilayer bound structures that are secreted by eukaryotic cells (ranging from plants to multicellular organisms). Similar vesicles can also be secreted by bacteria, but they differ from the eukaryote-derived EVs in composition and origin. Viruses do not produce EVs or similar vesicles. The EVs disclosed herein can be engineered to comprise one or more antigenic sequences of interest such as foreign peptides (e.g., virus-derived, bacterium-derived peptides or one or more components of allergenic compositions or venom). EVs can be engineered and produced from human cells transfected with an engineered plasmid that was transfected into cells.

Disclosed herein are compositions, including, but not limited to nucleic acid constructs, vectors, and cell lines, designed to produce a multi-component engineered EV. The compositions and methods disclosed herein allow for the preparation and use of engineered EVs to be self adjuvanting by engineering PAMP sequences adjacent to an antigenic sequence.

The compositions and methods disclosed herein allow for the preparation and use of engineered EVs that comprise a cell surface peptide that can be encoded by the same vector, that can not only increase the probability of an individual engineered EV to contain all three components (e.g. one or more antigenic sequences of interest, one or more PAMPs and one or more cell surface receptor binding peptides), but are also capable of binding to an immunologically relevant target cell. The compositions and methods disclosed herein can allow for increasing efficacy of an EV therapeutic/prophylactic entity by increasing the complexity of the target vector to include all essential components that can induce an immune response, adjuvant the activation by influencing innate immune mechanisms and target this mechanism to immunologically relevant cells as a one step process.

In an aspect, the engineered EVs disclosed herein can be generated by introducing plasmid constructs that drive the expression of the one or more antigenic sequences of interest (e.g., foreign peptides). The one or more antigenic sequences of interest can be tagged with one or more hydrophobic anchor sequences to ensure antigenic inclusion in membranes. The membrane hydrophobic anchor sequences can also include signals for protein ubiquitination to facilitate the incorporation of the engineered protein into the vesicles via the ESCRT machinery. The insertion of post-translational modified residues such as phosphorylated and/or ubiquitinated residues can be included during codon optimization so that the target immunomodulatory protein (e.g., foreign antigen, one or more antigenic sequences of interest) can be expressed at an effective level in the target cell.

The term "codon optimization" refers to specific modifications have been made to a gene that changes the gene sequence from the parent gene in the target organism including viral protein encoding sequences, bacterial protein encoding sequences, toxin encoding sequences in a manner that enhances expression in the specific target cell without affecting protein function in this case, which may be immunological activation. Such codon optimizations can be carried out to improve protein expression and to enhance protein folding and inclusion into vesicles (such as ubiquitination).

The expression construct (e.g., single nucleic acid construct) can also be engineered to co-express membrane associated marker peptides that can direct the vesicles for fusion with appropriate target membranes. The plasmid construct (e.g., single nucleic acid construct) can also be engineered to further comprise a separate pathogen-associated molecular pattern (PAMP) from an inducible promoter so that the EV can function as a self-contained immunomodulatory entity with a pre-defined mechanism of action. The plasmid construct (e.g., single nucleic acid construct) can also be made to comprise a selectable marker, such as gentamycin, that can used to generate a permanent cell line. Said permanent cell lines can be utilized as seed stocks for the generation of EVs for commercial purposes.

In an aspect, a plasmid vector (e.g. the pEV-vector; see FIG. 1) can comprise a set of expression entities involved in the generation of engineered extracellular vesicles that can be self-sustained for immunomodulatory activity. In an aspect, seed stock cell banks can be created from cells that took up the plasmid construct and express an antibiotic resistance marker (e.g., a selectable marker).

In an aspect, EV disclosed herein and designed as described herein can have the structure as shown in FIG. 1, having one or more components (e.g., one or more antigenic sequences of interest, one or more peptide and nucleic acid components common to all EVs generated by the parent cell line. In an aspect, induced expression of the antigen, the PAMPs and the membrane-associated ligand protein can result in the inclusion of new microRNA and protein components in the EV that can be considered uncommon or different from EVs produced from the parent cell line and can contribute to the immunomodulatory activity of the EVs As disclosed herein, engineered EVs comprise one or more viral peptides (e.g., one or more antigenic sequences of interest). In an aspect, EVs produced by specific cell type (or any other naturally occurring cell) may not contain this viral peptide (e.g., the one or more antigenic sequences of interest). In an aspect, the engineered EVs disclosed herein can be utilized as vaccine platforms as well as a novel class of immune modulators (e.g., adjuvants).

The EVs described herein can be produced by cultured human cells, and as such will be less reactogenic than whole, live attenuated viral vaccines, killed viral vaccines, subunit viral vaccines purified from serum samples (that may contain human derived pathogens), and subunit viral vaccines obtained from over expression systems including baculoviral or yeast based systems. In an aspect, the EVs described herein can be used as vaccines for administration to special groups including but not limited to immune-compromised individuals, elderly populations and infant populations.

In an aspect, the constructs described herein (e.g., single nucleic acid construct or EVs described herein) can also comprise immunomodulatory agents (e.g., PAMPS, Toll-like receptor (TLR) activating peptides) that can function as additive and/or synergistic enhancers of immunological activity of existing or novel antigens and, thus, be recognized as a novel group of immunomodulatory components (e.g., the nucleic acid construct).

The pEV-vector construct (e.g., single nucleic acid construct) described herein can permit the inclusion of immunoactive peptide constructs (e.g., one or more antigenic sequences of interest) derived from natural poisons and hyperallergens, including but not limited to reptile venom, insect venoms (e.g., spider venom) and toxins and aquatic dweller toxins (e.g., jellyfish toxins, snake toxins, honeybee toxin) as subcomponents. Such subcomponents may exhibit inflammatory regulatory activity without including other protein parts of the agents that may have deleterious consequences such as, for example, neurotoxic activity.

A common problem associated with vaccine platforms designed to protect against multiple related pathogens (e.g., multiple alphaviruses, dengue virus serotypes) is that one antigen can have immunosuppressive properties over another when simultaneously administered. The EVs described herein can permit rationalized vaccination regimens including but not limited to formulated cocktails, staggered vaccination timelines etc. The intrinsic immunomodulatory activity of the EVs described herein can permit their use as pre-priming strategies for sensitive vaccination regimens where heightened immune responsiveness may be required.

Subunit vaccines (e.g., purified peptides), when introduced into hosts directly, often run the risk of degradation due to circulating proteases. EVs as disclosed herein can provide a protective environment permitting longer bio-availability of circulating antigens.

EVs can be introduced by traditional injection routes, and can also be formulated for administration (e.g., delivery of EVs) including but not limited to inhalers, feed, topicals and prolonged-delivery patches. These later formulations and can permit the delivery of EVs to cattle, livestock feed, topical patches for animals recognized as pets, livestock, prolonged-delivery patches for personnel in high-risk situations such as emergency responsiveness and field activity.

EVs, by virtue of a surrounding lipid bilayer that is comparable to other lipid bilayer bound cells, can permit better fusion between the EVs and the target cells and hence increase the probability of cargo delivery. By engineering the expression of binding analytes (e.g., viral peptides; antigenic sequences of interest) that can specifically react with cell surface antigens/receptors, the specific receptor: analyte (e.g., viral peptides; antigenic sequences of interest) interaction can be exploited to improve peptide uptake.

For certain pathogens such as Malarial parasite, it is difficult to develop a common vaccine because the parasite exists as multiple stages. By identifying specific immunogenic proteins or peptides, however, vaccine cocktails or hybrid protein comprising EVs as disclosed herein can be designed.

In an aspect, the engineered EVs disclosed herein can be used as the vaccine candidate sought by federal agencies including Defense Threat Reduction Agency (DTRA) for the development of medical counter measures against New World alphaviruses. Such engineered EVs can provide a protective vaccine to the general public against old world alphaviruses (e.g., Chikungunya virus, an emerging infectious virus in the New World).

As the vaccine formulation of the EVs disclosed herein can be mild in reactogenicity, and can be useful for administration to immunocompromised populations, including, but not limited to HIV+ individuals, chemotherapy patients.

This use and development of the EVs described herein, as a therapeutic can be useful against multiple viral infectious agents where a) it was difficult to achieve complete attenuation of the virus, b) there is a high risk of reversion, c) there is immune interference from alternate viral peptides that can dilute the immune response to major viral antigenic peptides (e.g., surface glycoproteins), d) nonspecific immune responses to additional cell derived antigens exist in formulations when subunit vaccines are expressed in insect or yeast cells, and e) where multiple candidate vaccines to related families/groups of viruses are delivered simultaneously to elicit broad spectrum protection.

The platforms described herein can have inclusive immunomodulatory agents that can permit the platform to be utilized in a modular capacity to enhance responsiveness to other immunological agents as synergistic or additive tools.

The inclusion of specific membrane associated analytes (e.g., viral peptides antigenic sequences of interest) that can react with antibodies and/or cell surface expressed receptors can permit specific enrichment of the engineered vesicles from the native vesicle pool that does not include the antigenic sequences of interest. This can allow the production of pure populations of engineered EVs for commercial purposes. Additionally, such pure populations can be characterized for their composition more accurately for ease of regulatory approval.

The utility of EVs as vaccine platforms has been demonstrated for cancer. The utility, however, of EVs as vaccines for acute and chronic viral infections by the inclusion of individual viral peptides in EVs has not been shown. EVs as disclosed herein differ significantly from bacterial cell wall-derived vesicles which referred to as outer membrane vesicles (OMVs). OMVs originate naturally from bacterial cell walls, and are also highly variable. OMVs generated in one culture supernatant from one type of a bacterial culture will not be uniform in their composition of bacterially derived peptides.

Described herein are methods and compositions comprising EVs that include one or more viral peptides (e.g., one or more antigenic sequences of interest). Aspects of the disclosure comprise inclusion of the one or more viral peptides (e.g., one or more antigenic sequences of interest) in the EVs. Additional aspects include, for example: a) formulation strategies; b) proof of concept confirmations in at least two animal models depending on availability of appropriate animal models (available for alphaviruses); c) mechanism of action that drives immune responses (proteomic characterization); d) ability of EVs to establish long term immune memory (epigenetic modifications; CD4/CD8 responses); immune modulators and immune markers (immunoglobulins, cytokine responses); e) scale up strategies without compromising product efficacy; f) lot to lot uniformity; g) potential adverse events associated with EV introduction; and h) alternate delivery mechanisms and relative efficacy of immune responses.

In an aspect, the compositions and/or methods disclosed herein comprise one or more viruses (e.g., one or more antigenic sequences of interest). In an aspect, methodologies that integrate processes to enable self-adjuvanting action and mechanisms to impart individuality to the candidate (such as tagging with proprietary amino acid tags (e.g., one or more hydrophobic anchor sequences)) are disclosed.

Figure 3:
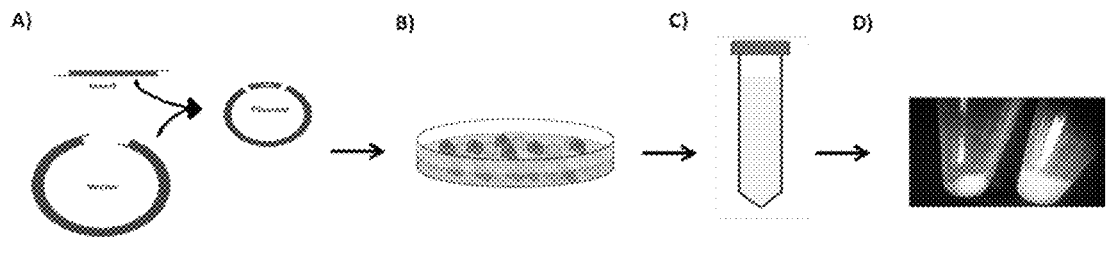
FIG. 3 is a schematic showing the steps involved in producing extracellular vesicles (EVs).
Figures 4A, 4B:
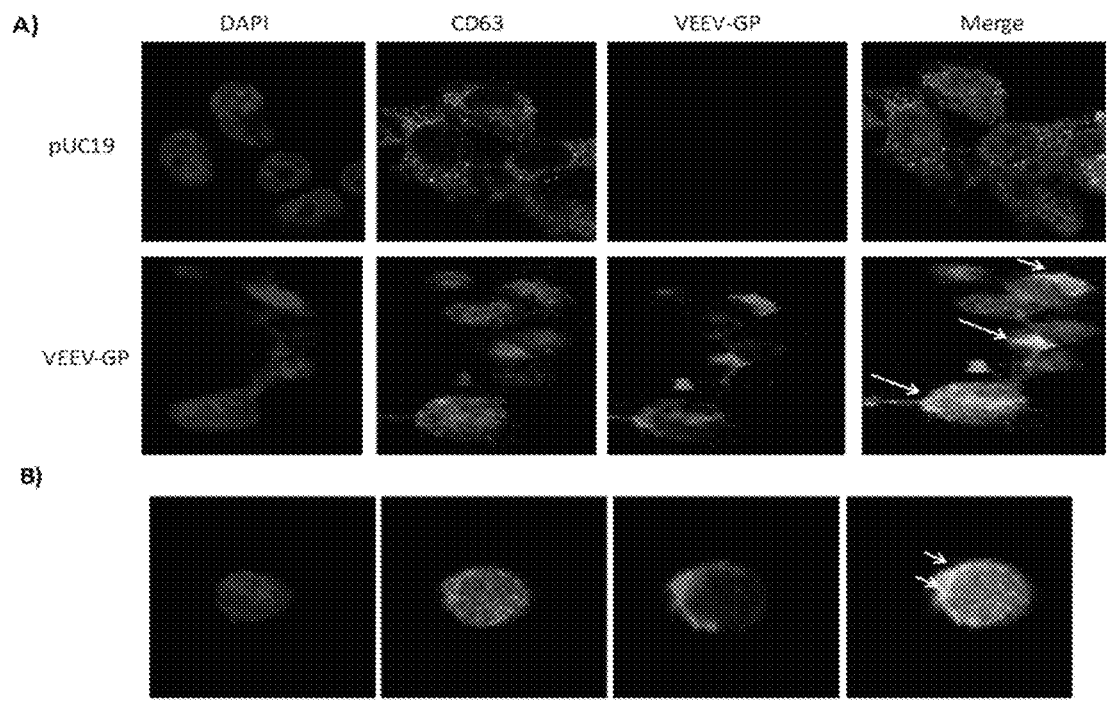
FIGS. 4A-B show data that confirms the inclusion of an antigenic sequence of interest in an extracellular vesicle (EV).
Figures 6A, 6B, 6C, 6D:
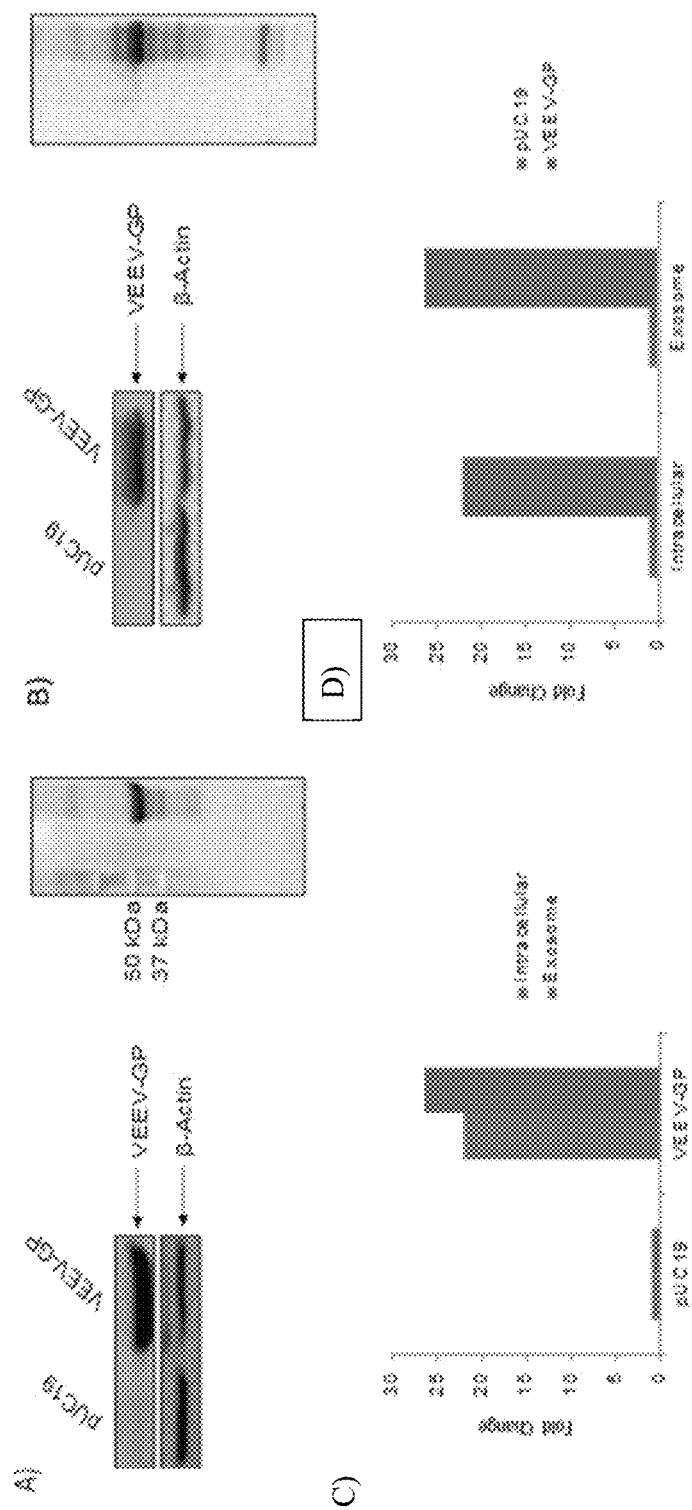
FIGS. 6A-D show data that confirms that engineered extracellular vesicles (EVs) as described herein can include antigenic sequences of interest.
Figure 9:
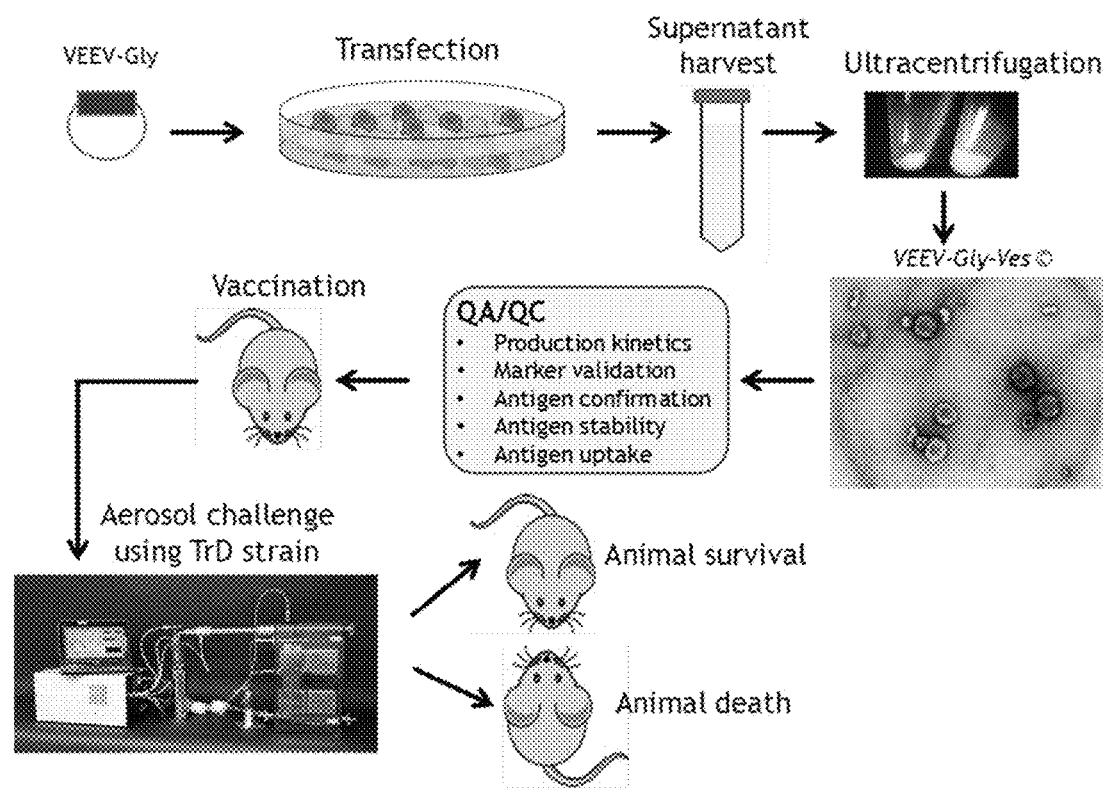
Figure 10A:
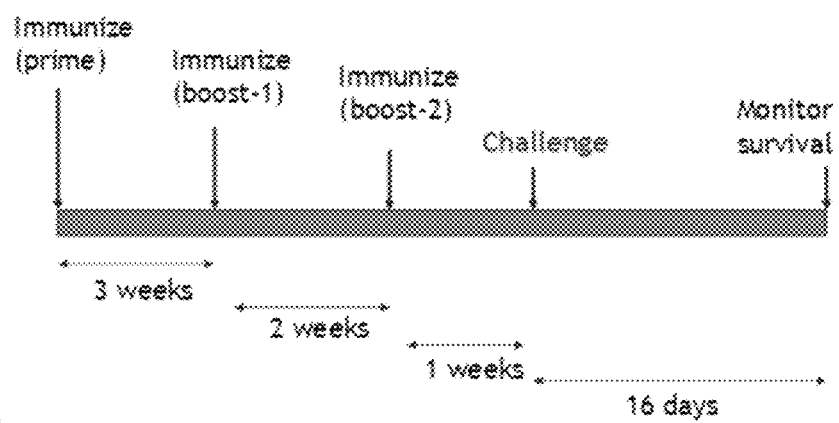
FIGS. 10A-B show engineered extracellular vesicles (EVs) expressing a viral glycoprotein can protect mice from a lethal aerosol challenge associated disease and death.
Figure 10B:
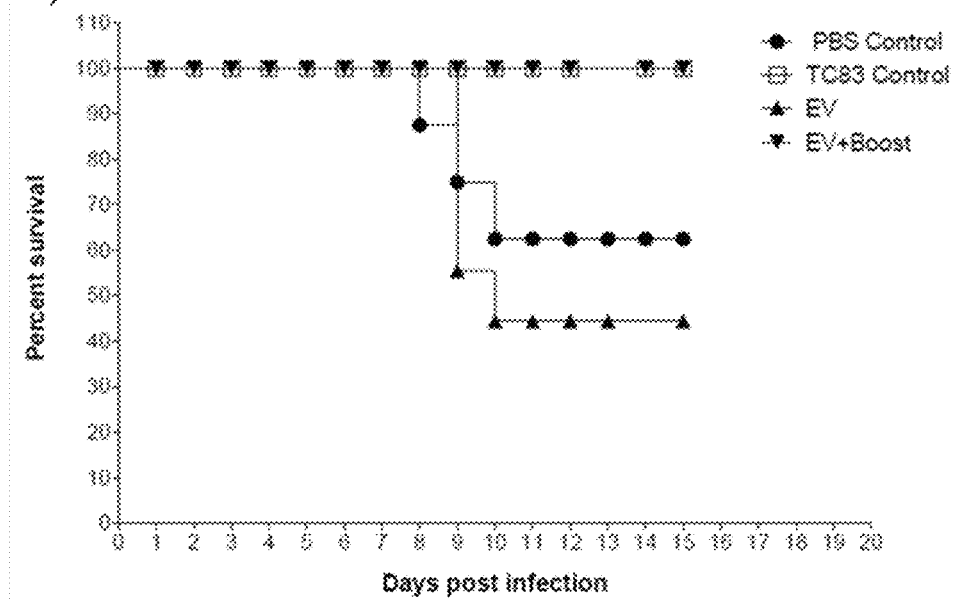

In an aspect, the engineered vesicles as disclosed herein comprises foreign antigen (e.g., one or more antigenic sequences). The foreign antigen (e.g., one or more antigenic sequences) can be due to the expression of a gene from a transfected plasmid as shown in the FIG. 3. FIG. 3 demonstrates that an engineered EV can be generated by artificially introducing a gene into a host cell. Further evidence of the inclusion of the immunoreactive foreign peptide in the EVs is shown in FIG. 4 demonstrating the colocalization of the foreign peptide (e.g., one or more antigenic sequences) with the native tetraspanin anchor protein CD63. This method can be fine-tuned using permanent cell lines generated by including a selectable marker in the same plasmid construct (see the pEV-Vector construct in FIG. 3). The platform disclosed herein can be used as a research tool to understand mechanisms by which foreign peptides included in EVs as a part of natural processes such as infections impact disease progression, host survival (see FIG. 9 and FIGS. 10A-B) and responsiveness to therapeutics. The platform can also be utilized to understand mechanisms behind host derived biomarkers during the infectious process.

The platform has commercial applications beyond its utility as a research tool. By the unique inclusion of viral surface peptides, the EVs can be utilized to generate an immune response in the host (vaccine). By harnessing the inherent immunogenic nature of included analytes (e.g., viral peptides, antigenic sequences of interest) and by leveraging their ability to uniquely modify pathogen recognition receptors, the EVs can be used as adjuvants or generic modulators of immune responsiveness.

In an aspect, the platform described herein can extend to multiple infectious agents. For example, activation of PAMP receptors and intracellular signaling activation can be potent additions to increase the spectrum of application of these engineered EVs.

The engineered EVs can be specifically utilized as vaccines and as adjuvants. In an aspect, an EV contains the outer membrane glycoprotein derived from Venezuelan Equine Encephalitis Virus (VEEV). VEEV is a pathogen that causes natural infections in South America. VEEV is also an easily aerosolizable virus and is stable, retains infectivity as an aerosol. For that reason, it has bioterrorism potential and is classified as a select agent. There are currently no FDA approved vaccines or therapeutics to treat/protect from VEEV infections. There is a limited use vaccine which is plagued by reactogenicity issues. There is a killed vaccine available which has very poor immunogenic potential and is used only as a booster candidate. So, there is a need for a robust vaccine without the undesirable reactogenic effects. EVs can provide an answer to that problem.

VEEV is one of a related group of viruses called New World alphaviruses. New World alphaviruses include Eastern Equine Encephalitis Virus (EEEV) and Western Equine Encephalitis Virus (WEEV) in addition to VEEV. We will generate the EVs with the EEEV and WEEV glycoproteins as well with the intention of developing an EV cocktail for New World alphavirus infections.

Alphaviruses are known to activate immune responses. The glycoproteins themselves, inherent to being immunogenic, can be utilized as adjuvants to enhance immunogenicity. This can be particularly applicable to the killed alphavirus vaccine that is known to be poorly immunogenic. This option is better than traditional nonspecific adjuvants because known adjuvants such as alum, LPS-based adjuvants, double-stranded RNA/DNA adjuvants have multiple undesirable side effects with toxicity being an important concern.

In an aspect, engineered EVs that express a surface glycoprotein of New World alphaviruses are disclosed. The same methodology can be extended to other infectious agents to induce protective immune responses. Such engineered EVs with immunomodulatory activity can be applicable to noninfectious disease states where immunomodulatory activity can increase health benefits to the host. For example, more than one (e.g., multiple) antigenic sequence of interest can be administered to a subject to confer broad spectrum protection to a host. It is possible when more than one antigenic sequences of interest are administered to a subject that immunological interference may skew the immune system response toward one antigen over another. Thus, in an aspect, engineered EVs as disclosed herein can be generated with varying levels of expression of individual antigenic peptides. In an aspect, the peptides expressed from the single nucleic acid constructs as disclosed herein can be produced with varying levels of individual antigenic sequences of interest. The engineered EVs or single nucleic acid constructs as described above can be administered to a subject to progressively alter an immune system response to favor a single antigen. Such treatment regimens can be used to elicit an immunological response against more than one antigen safely.

Besides the alphavirus vaccines, an aspect of the disclosure comprises similar EVs for other viruses as well including flaviviruses, coronaviruses, retroviruses, paramyxoviruses. EVs can also be produced against biological toxins for which peptide sequences are known. The engineered EVs disclosed herein can be extended to biological toxins. EVs can also be utilized as delivery mechanisms to generate reagents such as monoclonal antibodies.

The engineered EVs, by virtue of being inclusive of other immunomodulatory entities, such as membrane expressed PAMPs, can be utilized as additive/synergistic immunoenhancing agents. By incorporating non-native immunostimulatory molecules such as peptide entities (e.g., one or more antigenic sequences of interest that can be partial sequences of the entire peptide entity) from animal/insect venoms and poisons, enhanced immune activation can be achieved while bypassing toxigenic outcomes.

The strength of the technology described herein lies in the simplicity of production, ease to train personnel, ease to mix and match vesicles, ease to create hybrid peptides, ease of delivery (including, for example, slow release patches) and combining such delivery methods with other administration methods including but not limited to subcutaneous and subdermal injections. Once the pipeline is standardized, the EVs can be produced in a cost effective manner which can lower down the cost per dose. As EVs can continue to be immunogenic even if they are not functionally active, they can be immunogenic over long periods of time under standard storage conditions unlike live vaccines (i.e., the yellow fever vaccine, possibly the most efficacious and safe live attenuated vaccine can be considered "useable" only for up to 8 hours from the time the vial was opened, and only if during that time, it was kept at 4 degrees).

An aspect of the disclosure comprises specific subportions of the entire peptide that may be subcloned in an attempt to hone in the immunogenic moiety (away from dilution due to multiple antigenic peptide (e.g., one or more antigenic sequences) and/or structural features of the whole peptide that may mask the immunogenic peptide).

Compositions

Disclosed herein are single nucleic acid constructs. The single nucleic acid constructs can comprise a vector. In an aspect, the vector can be a viral vector. In an aspect, the vector comprises a first nucleic acid sequence. The first nucleic acid sequence can comprise one or more antigenic sequences of interest, one or more spacer sequences and one or more hydrophobic anchor sequences, operably linked to a first transcriptional control element. In an aspect, the vector comprises a second nucleic acid sequence. The second nucleic acid sequence can comprise one or more pathogen-associated molecular pattern (PAMP) sequences. The one or more PAMP sequences can be operably linked to a second transcriptional control element. In an aspect, the vector can comprise a third nucleic acid sequence. The third nucleic acid sequence can comprise one or more cell surface receptor binding sequences. The one or more cell surface receptor binding sequences can be operably linked to a third transcriptional control element. In an aspect, the vector can comprise a selectable marker.

In an aspect, a cell line comprises the single nucleic acid construct described herein.

In an aspect, the transcriptional control elements can be regulatable. In an aspect, at least one of the transcriptional control elements is regulatable. The first, second and third transcriptional control elements can be the same, different or a combination thereof. The transcriptional control elements can be oriented in the same or opposite directions.

Regulatable transcriptional control elements can optionally comprise a regulator target sequence. Regulator target sequences can comprise nucleic acid sequence capable of being bound to a binding domain of a fusion protein expressed from a regulator construct such that a transcription repression domain acts to repress transcription of a nucleic acid sequence contained within the regulatable transcriptional control element. Regulator target sequences can comprise one or more tet operator sequences (tetO). The regulator target sequences can be operably linked to other sequences, including, but not limited to, a TATA box or a GAL-4 encoding nucleic acid sequence.

The expression of any of the nucleic acid sequences disclosed herein can be regulatable.

In an aspect, the transcriptional control element can be inducible. In an aspect, at least one of the transcriptional control elements is inducible. The first, second and third transcriptional control elements can be the same, different or a combination thereof.

In aspect, the first, second and third transcriptional control elements can be regulatable, inducible or a combination thereof.

The term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of DNA to a transcriptional control element refers to the physical and functional relationship between the DNA and promoter such that the transcription of such DNA is initiated from the promoter by an RNA polymerase that specifically recognizes, binds to and transcribes the DNA.

The transcriptional control element can be a promoter. In an aspect, the promoter can be a mammalian cell active promoter (e.g., SV40, CMV, SP6, T7); a yeast active promoter (e.g., GAL4); a bacteria active promoter (e.g., Lac); or a baculovirus/insect cell active promoter (e.g., polyhedron). In an aspect, the transcriptional control element can be an inducible promoter. Examples of inducible promoters include but are not limited to tetracycline inducible system (tet); heat shock promoters and IPTG activated promoters.

In an aspect, the first nucleic acid sequence can comprise one or more antigenic sequences of interest. The one or more antigenic sequences of interest can encode one or more peptides derived from a virus, a toxin, a bacterium or an allergen or a combination thereof. The one or more peptides encoded by the one or more antigenic sequences of interest can elicit an immune system response. In an aspect, the one or more peptides derived from a virus, a toxin, a bacterium or an allergen is separated by one or more spacer sequences or is contiguous. In an aspect, the one or more peptides derived from a virus, a toxin, a bacterium or an allergen is a full sequence, a fragment sequence or a combination thereof.

Examples of viral peptides include but are not limited to surface expressed glycoproteins of enveloped viruses; secreted proteins that may not be included as part of mature virions, but may be released from cells along with mature virions (e.g., NS1 protein from Dengue virus). Viral peptides can also include protein coats of viruses that may be internal to outer envelope layers (e.g., capsid proteins for enveloped viruses).

In an aspect, the one or more antigenic sequences of interest can encode one or more peptides derived from a virus. Generally, acutely infectious viruses that are enveloped can be used. The viruses that can be used herein include infectious agents that infect humans and animals (e.g., terrestrial and aquatic). Examples of enveloped viruses that infect humans and cause disease and whose antigenic sequences can be incorporated into the vector described herein include but are not limited to retroviruses, togaviridae, flaviviridae, arenaviridae, orthomyxovirus, rhabdovirus, reovirus, and picornaviruses. Examples of DNA viruses include but are not limited to herpes virus, adenovirus, poxvirus. In an aspect, the virus can be a retrovirus, togaviridae, flaviviridae, arenaviridae, orthomyxovirus, rhabdovirus, reovirus, picornavirus, herpes, adenovirus or poxvirus.

Examples of toxin peptides include but are not limited to E. coli, Hemolysin; RTX domain containing exotoxins (e.g., hemolysins and leukotoxins); *Bordetella pertussis* adenylate cyclase toxin; and secreted components of bacteria that are toxigenic and may contribute to disease pathology. Other toxins include but are not limited to aquatic dweller toxins (e.g., jellyfish toxins, snake toxins).

Examples of bacterial peptides include but are not limited to protein components of the outer cell wall and/or membrane of gram positive and gram negative bacteria. Bacterial components of the outer membrane vesicles produced by bacterial cells can also be included as antigenic components (e.g., antigenic sequence of interest) in the multicomponent vector system (e.g., single nucleic acid construct described herein) as a way to neutralize extracellular communication between bacteria in the infected host as well as to control bacterial multiplication itself. Examples of bacteria are known to one of ordinary skill in the art.

Examples of allergens include but are not limited to small subsections of the protein that have the ability to induce immune stimulation (e.g., trigger or elicit an immune system response). For example, components of insect venom can be included. In an aspect, the allergen is a venom. Examples of venom include but are not limited to reptile venom, insect venoms (e.g., spider venom, honey bee venom), fish venoms, therapsida and other invertebrate venoms.

In an aspect, the one or more antigenic sequences of interest are separated by a spacer sequence. In an aspect, the one or more antigenic sequences of interest are contiguous. In an aspect, the one or more antigenic sequences of interest are contiguous or separated by a spacer sequence.

The spacer sequence can be located between the separate individual antigenic sequences of interest, the one or more antigenic sequences and the one or more hydrophobic anchor sequences, the one or more hydrophobic anchor sequences, and individuals PAMPS. Spacer sequences serve to permit inclusion of the individual sequences, for example, PAMP motifs, as surface expressed entities on the extracellular vesicle. Generally, spacer sequences serve to link sequences together without interfering with their intended or unintended function. In the absence of a spacer sequence, the result can be transmembranal sequence with intracellular regions, such the PAMP sequences, for example, will not be expressed as contiguous motifs expressed on the cellular surface. Further, the spacer sequences permit a special separation between the surface expressed PAMP motifs, for example such as there is no steric hindrance while interacting with immunogenic cells. The spatial separation of the PAMP motifs, for example can permit multiple immunogenic cells to interact with a single extracellular vesicle via more than one, spatially placed PAMP. The PAMP sequences are used as an example that can apply to any of the sequences described herein that can be separated by one or more spacer sequences.

In an aspect, the one or more antigenic sequences of interest is contiguous with the one or more hydrophobic anchor sequences. The one or more hydrophobic anchor sequences can be a nucleic acid sequence that is capable of encoding an amino acid anchor sequence. The amino acid anchor sequence can comprise a series of contiguous hydrophobic amino acids. Hydrophobic amino acids are known to one of ordinary skill in the art. Examples of hydrophobic amino acids include glycine, alanine, valine, leucine, isoleucine, proline, phenylalanine, methionine and tryptophan. In an aspect, the one or more hydrophobic anchor sequences comprises a nucleic acid sequence capable of encoding one or more ubiquitin proteins. In an aspect, the peptide encoded by the one or more hydrophobic anchor sequences described herein comprises between seven to ten amino acids. The hydrophobic anchor sequences described herein can comprise 1, 2, 3, 4, 5, 10, 15 amino acids or any number in between.

Generally, hydrophobic regions serve to permit membrane insertion of one or more of the peptides encoded by the nucleic acid constructs described herein (e.g., one or more antigenic sequences of interest), and can include well documented peptide structures such as alpha helical bundles. Many proteins that are anchored to endoplasmic reticulum and secreted multivesicular bodies can be used. Transmembrane regions of single pass and multipass eukaryotic and/or bacterial membrane proteins may also be used.

In an aspect, the second nucleic acid sequence comprises one or more pathogen-associated molecular pattern (PAMP) sequences operably linked to a second transcriptional control element. In an aspect, the expression of the one or more pathogen-associated molecular pattern (PAMP) sequences is regulatable. In an aspect, one or more PAMP sequences are separated by a spacer sequence or is contiguous.

In an aspect, the one or more pathogen-associated molecular pattern sequences is capable of encoding one or more pathogen-associated molecular patterns. The one or more pathogen-associated molecular patterns can be a complete sequence, a fragment (or partial) sequence or a combination thereof of one or more PAMPs. The complete sequence, a fragment sequence or a combination thereof of the one or more PAMPs can be separated by one or more spacer sequences.

PAMPs are molecules associated with pathogens that are recognized by cells of the innate immune system. PAMPs can be referred to as small molecular motifs conserved within a class of microbes but distinguishable from host molecules. PAMPs are recognized by Toll-like receptors (TLRs) and other pattern recognition receptors in both plants and animals. TLRs are a type of pattern recognition receptor. Examples of PAMPs include but are not limited to glycans and glycoconjugates.

PAMPs activate innate immune system and can illicit or trigger an immune response. Activation of PAMPs can lead to protection of the host from infection, by identifying some conserved non-self molecules. An example of a class of PAMPs is bacterial lipopolysaccharides (LPS). LPSs are endotoxins found on the cell membranes of bacteria and are recognized by TLRs (e.g., TLR4). Examples of PAMPs include bacterial flagellin (recognized by TLR5), lipoteichoic acid from gram-positive bacteria, peptidoglycan, and nucleic acid variants typically associated with viruses, such as double-stranded RNA (recognized by TLR3) or unmethylated CpG motifs (recognized by TLR9.

Generally, any sequence capable of activating TLRs (including those that are included in the plasma membrane as well as those that may be intracellular) can be used herein. Synthetic mimics that capture the features of the natural TLR agonist can be used as part of the single nucleic acid construct. In an aspect, PAMP sequences can also include activators of the inflammasome and Nod-like receptor agonists such as bacterial peptidoglycans or their synthetic mimics. In an aspect, activators of RIG-I receptors and C-type lectin receptors can also be utilized as natural compounds or as their synthetic mimics.

In an aspect, the third nucleic acid sequence can comprise one or more cell surface receptor binding sequences operably linked to a third transcriptional control element. In an aspect, expression of the one or more cell surface receptor binding sequences is regulatable. In an aspect, the one or more cell surface receptor binding sequences is capable of encoding one or more cell surface receptor binding peptides.

In an aspect, the one or more cell surface receptor binding peptides are capable of binding to T-cell, B-cell, macrophage, dendritic cell surface receptors or a combination thereof.

The cell surface receptor binding sequences serve to bind to or increase binding to immune system cells or immune reactive cells. Cell surface receptor binding sequences are capable of triggering or eliciting or enhancing an immune system response. Examples of cell surface receptor binding proteins include but are not limited to C-type lectins, MMR, CD206, and DC-SIGN. For example, C-type lectins can bind to a surface C-type lectin receptor on macrophages or dendritic cells.

In an aspect, the single nucleic acid construct described herein comprises a selectable marker. In an aspect, the selectable marker is an antibiotic resistance gene. Examples of suitable markers (e.g., antibiotic resistance genes) include but are not limited to gentamycin, hygromycin (e.g., hygromycin A, hygromycin B), puromycin, Blasticidin S, Zeocin or G418 (Geneticin). When such selectable markers are successfully transferred into a mammalian host cell, the transformed mammalian host cell can survive if placed under selective pressure. Selectable markers can also be used as a reporter to identify those animals comprising a sequence of interest.

Disclosed herein are cells that produce extracellular vesicles. The extracellular vesicles can comprise one or more antigenic peptides, one or more hydrophobic anchor peptides; one or more PAMPs; one or more cell surface receptor binding peptides and a selectable marker as described herein. In an aspect, the one or more antigenic peptides is tetraspanin. In an aspect, the selectable marker is gentamycin.

Disclosed herein are engineered extracellular vesicles comprising one or more antigenic peptides, one or more hydrophobic anchor peptides; one or more PAMPs; one or more cell surface receptor binding peptides and a selectable marker as described herein.

The EVs disclosed herein can be administered to pets and livestock. In an aspect, the appropriate host based cell lines can be used. The EVs disclosed herein can also be administered to human subjects (e.g., human patients). In an aspect, the EVs disclosed herein can be administered to a subject for a specific therapy. For example, one approach is to isolate the subject's own cells (e.g., the patient's own tumor cells, stem cells). The subject's own cells can be used those to generate EVs that are subject cell specific. The subject's own cells can be combined with a cell line disclosed herein transfected to express any of the nucleic acid sequences described herein. This approach can be used to treat, manage or prevent cancer. In an aspect, the EVs and single nucleic acid constructs described herein can comprise one or more nucleic acid sequences derived from a cancer cell. The cancer cell can be from a cell line or from the subject's own cell or from another subject's own cell. In an aspect, cell line or one or more nucleic acid sequences described herein is an umbilical cord-derived stem cell.

Synthetic mimics that capture any of the features of any of the components of the single nucleic acid construct as disclosed herein can be used as part of the single nucleic acid construct, EV or composition.

Methods

Single Nucleic Acid Constructs.

Disclosed herein are methods of producing the extracellular vesicles described comprising the following steps: (1) introducing a first nucleic acid sequence, wherein the first nucleic acid sequence comprises one or more antigenic sequences of interest, one or more spacer sequences and one or more hydrophobic anchor sequences, operably linked to a first transcriptional control element; (2) introducing a second nucleic acid sequence, wherein the second nucleic acid sequence comprises one or more pathogen-associated molecular pattern sequences operably linked to a second transcriptional control element; (3) introducing a third nucleic acid sequence, wherein the third nucleic acid sequence comprises one or more cell surface receptor binding sequences operably linked to a third transcriptional control element; (4) introducing a selectable marker; and (5) maintaining the cell under conditions that allow expression of (a), (b), (c) and (d) of the extracellular vesicle. The one or more antigenic sequences of interest can be a nucleic acid sequence encoding one or more peptides derived from a virus, a toxin, a bacterium or an allergen. One of ordinary skill in the art can determine the proper solvent(s) required and calculate the concentrations of any of the ingredients involved in each step.

Any known cell transfection technique can be carried out for the method of making the cells or EVs described herein. Generally for in vitro methods, cells are incubated (i.e., cultured) with the constructs or vectors in an appropriate medium under suitable transfection conditions, as is well known in the art. For example, methods such as electroporation and calcium phosphate precipitation can be used.

Any known cloning technique can be carried out for the method of making the single nucleic acid constructs described herein. Vectors can be prepared and maintained under standard conditions, using, for example, synthetic genetic constructs comprising any of the nucleic acid sequences disclosed herein.

Pharmaceutical Compositions.

As disclosed herein, are pharmaceutical compositions, comprising one or more of the single nucleic acid constructs, cell lines or vesicles described herein and a pharmaceutical acceptable carrier. In some aspects, the pharmaceutical composition is formulated for intravenous, subcutaneous, transdermal or nasal administration. The compositions of the present disclosure also contain a therapeutically effective amount of one or more of the single nucleic acid constructs, cell lines or vesicles as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for parenteral administration. Pharmaceutical compositions prepared for parenteral administration include those prepared for intravenous (or intra-arterial), intramuscular, subcutaneous, intraperitoneal, transmucosal (e.g., intranasal, intravaginal, intradermal or rectal), or transdermal (e.g., topical) administration. Aerosol inhalation can also be used to deliver the single nucleic acid constructs described herein. Thus, compositions can be prepared for parenteral administration that includes single nucleic acid constructs dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment.

Disclosed herein are methods of preventing or treating an infection or a disease, the method comprising: (a) identifying a subject in need of prevention or treatment of an infection or a disease; and (b) administering to the patient a therapeutically effective amount of the pharmaceutical composition comprising one or more of the single nucleic acid constructs, cell lines or vesicles as described herein. The single nucleic acid constructs comprise a vector. The vector can comprise a first nucleic acid sequence, wherein the first nucleic acid sequence comprises one or more antigenic sequences of interest, one or more spacer sequences and one or more hydrophobic anchor sequences, operably linked to a first transcriptional control element; a second nucleic acid sequence, wherein the second nucleic acid sequence comprises one or more pathogen-associated molecular pattern (PAMP) sequences operably linked to a second transcriptional control element; and a third nucleic acid sequence, wherein the third nucleic acid sequence comprises one or more cell surface receptor binding sequences operably linked to a third transcriptional control element. In an aspect, the pharmaceutical composition further comprises a pharmaceutically acceptable carrier. In an aspect, the one or more pathogen-associated molecular patterns are separated by one or more spacer sequences or is contiguous.

The pharmaceutical compositions described above can be formulated to include a therapeutically effective amount of one or more of the single nucleic acid constructs, cell lines or vesicles as disclosed herein. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of infection or disease.

In an aspect, the composition described herein can be formulated as a vaccine preparation. As used herein, a "vaccine" or a "composition for vaccinating a subject" specific for a particular pathogen means a preparation, which, when administered to a subject, leads to an immunogenic response in a subject.

As used herein, an "immunogenic" response or an "immune system response" is a response that confers upon the subject protective immunity against a pathogen (e.g., virus, bacteria, toxin or allergen). Without wishing to be bound by theory, it is believed that an immunogenic response can arise from the generation of neutralizing antibodies (i.e., a humoral immune response) or from cytotoxic cells of the immune system (i.e., a cellular immune response) or both. As used herein, an "immunogenic antigen" is an antigen which induces an immunogenic response when it is introduced into a subject, or when it is synthesized within the cells of a host or a subject. As used herein, an "effective amount" of a vaccine or vaccinating composition is an amount which, when administered to a subject, is sufficient to confer protective immunity upon the subject. Historically, a vaccine has been understood to contain as an active principle one or more specific molecular components or structures which comprise the pathogen, especially its surface. Such structures can include surface components such as peptides, complex carbohydrates, and/or complex lipids which commonly are found in pathogenic organisms.

As used herein, however, it is to be stressed that the terms "vaccine" or "composition for vaccinating a subject" extend the conventional meaning summarized in the preceding paragraph. As used herein, these terms also relate to the antigenic sequence of interest of the present disclosure or to compositions containing the one or more antigenic sequences of interest.

The pharmaceutical compositions described herein can be administered to the subject (e.g., a human patient) in an amount sufficient to delay, reduce, or preferably prevent the onset of clinical disease or signs or symptoms of an infection. Accordingly, in some aspects, the patient is a human patient. In therapeutic applications, compositions are administered to a subject (e.g., a human patient) already with or diagnosed with an infection or an infectious disease or suspected of having an infection or infectious disease in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is one among several that can be achieved. As noted, a therapeutically effect amount includes amounts that provide a treatment in which the onset or progression of the infection is delayed, hindered, or prevented, or the infection or a symptom of the infection is ameliorated. One or more of the symptoms can be less severe. Recovery can be accelerated in an individual who has been treated.

In an aspect, the infection is caused by a virus, bacterium, allergen, or a toxin. In some aspects, the infection is caused by an infectious agent including acute viral infections, chronic viral infections, and bacterial infections. An "acute viral infection" is characterized by a rapid onset of clinical signs or symptoms of an infection or disease, and often has a relatively brief period of symptoms followed by resolution in days. "Chronic viral infections" can be persistent involving one or more stages of silent and productive infection without killing or causing damage to host cells. Chronic infections include latent, chronic and slow infections. An acute viral infection can become a chronic viral infection.

The one or more of the single nucleic acid constructs, cell lines or vesicles described herein can be used to induce or enhance an immune system response in a subject (e.g., human or animal). In an aspect, the one or more of the single nucleic acid constructs, cell lines or vesicles described herein can be used to treat or prevent cancer. The antigenic sequences of interest can be modified, mutated or altered peptides that are expressed in transformed cells as part of an immunotherapeutic regimen.

In an aspect, the one or more of the single nucleic acid constructs, cell lines or vesicles described herein can be used to treat or prevent infections or diseases caused by one or more of following: enveloped viruses, DNA viruses, RNA viruses. In an aspect, infections or diseases in pets including terrestrial and aquatic animals can be treated. Additional infections or diseased that can be treated by the constructs and compositions disclosed herein include but are not limited to bacterial infections (e.g., meningococcal infections, streptococcal infections and those caused by multiple drug resistant bacteria). In an aspect, both intracellular and extracellular bacterial infections can be treated by the constructs and compositions disclosed herein.

Disclosed herein are methods of treating a subject at risk for or having a disease. The method can comprise administering to the subject an effective amount of the one or more of the single nucleic acid constructs, cell lines or vesicles disclosed herein. In an aspect, disease is an infectious disease caused by a virus, bacteria, allergen or toxin. In an aspect, the disease is cancer. In an aspect, the single nucleic acid construct can be administered intravenously, subcutaneously, transdermally, or nasally.

Amounts effective for the uses described herein can depend on the severity of the infection or the potential exposure or the cancer or infectious disease and the weight and general state and health of the subject, but generally range from about 0.05 μg to about 1000 μg (e.g., 0.5-100 μg) of an equivalent amount of the single nucleic acid construct or engineered extracellular vesicle per dose per subject. Suitable regimes for initial administration and booster administrations are typified by an initial administration followed by repeated doses at one or more hourly, daily, weekly, or monthly intervals by a subsequent administration. For example, a subject can receive a single nucleic acid construct in the range of about 0.05 to 1,000 μg equivalent dose one or more times per week (e.g., 2, 3, 4, 5, 6, or 7 or more times per week). For example, a subject may receive 0.1 to 2,500 μg (e.g., 2,000, 1,500, 1,000, 500, 100, 10, 1, 0.5, or 0.1 μg) dose per week. A subject can also receive one or more of the compositions described herein (e.g. a single nucleic acid construct, cell line, or engineered extracellular vesicle) in the range of 0.1 to 3,000 μg per dose once every two or three weeks. A subject can also receive 2 mg/kg every week (with the weight calculated based on the weight of the single nucleic acid construct).

The total effective amount of one or more of the compositions described herein (e.g. a single nucleic acid construct, cell line, or engineered extracellular vesicle) in the pharmaceutical compositions disclosed herein can be administered to a mammal (or terrestrial or aquatic) as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of the one or more of the compositions described herein (e.g. a single nucleic acid construct, cell line, or engineered extracellular vesicle) present within the compositions described herein and used in the methods as disclosed herein applied to mammals (e.g., humans) and other animals can be determined by one of ordinary skill in the art with consideration of individual differences in age, weight, and other general conditions (as mentioned above).

The compositions described herein can be administered as a post-exposure prophylactic treatment. Further, pre-exposure preventive administration is within the scope of the present disclosure. In an aspect, one or more of the compositions described herein (e.g. a single nucleic acid construct, cell line, or engineered extracellular vesicle) can be administered as a combination therapy. For example, compositions disclosed herein can be administered along with (including before, simultaneously or sometime thereafter) with immunological and/or small molecule therapeutic strategies.

EXAMPLES

Example 1: Extracellular Vesicles as Vaccine Candidates Against Alphaviruses

This example shows the methods to develop extracellular vesicles (EVs) that express the Venezuelan Equine Encephalitis Virus (VEEV) structural proteins (E1 and E2) on the membrane surface. The application of such engineered EVs as vaccine candidates can be carried out either independently or in conjunction with additional candidates. EVs are nano- and micro-sized vesicles that are produced by all cell types. EVs contain both RNA and peptides and have been implicated in information transfer between cells. They are generated in vivo by multiple cell types and have been demonstrated to fuse with multiple target cells to deliver their cargo. Research has previously demonstrated that EVs arising from virus-infected cells carry virus-derived components including envelop glycoproteins. Findings from the Gould laboratory have demonstrated that intracellular proteins can be engineered to be secreted in vesicles and can be localized to membranes. A recent report by Dupuy et al has demonstrated the utility of a DNA vaccine candidate that expresses VEEV structural proteins in eliciting an immune response in non-human primate models. This led to the instant hypothesis that EVs engineered to express alphavirus structural proteins on the surface will induce an immune response in the host and hence be a vaccine candidate. EVs were engineered to express VEEV structural proteins. EVs were isolated and enriched from transfected cells, characterized and validated and finally tested the EVs for induction of an immune response in a murine model when challenged with virulent VEEV. The results were a novel vaccine platform for VEEV that can complement the recently developed DNA vaccine platform and can be developed for use either independently or in conjunction with the DNA vaccine.

Background and Significance.

Alphaviruses, including Venezuelan Equine Encephalitis Virus (VEEV), Eastern Equine Encephalitis Virus (EEEV), and Western Equine Encephalitis Virus (WEEV), cause disease in equine and humans that exhibit overt encephalitis in a significant percentage of cases. VEEV can also cause infection by the respiratory route and has previously been weaponized. All of the encephalitic alphaviruses are considered category B agents. There is no FDA approved therapeutics available for the treatment of these infections. Development of effective vaccines to confer protection from alphavirus infections is an important avenue of research.

EVs are nano-sized and/or micro-sized vesicles that are produced by multiple cell types. EVs have generated a lot of attention recently as key mediators of disease progression as they have been demonstrated to contain cargo that is associated with disease, and of specific interest in the case of infectious diseases. EVs are being considered attractive vaccine candidates because they have a history of being activators of immune responses. As an example, in a recent report by Vallhov et al, the authors show that expression of EBV glycoprotein in EVs elicits immune responses from recipient cells. According to Chaput et al., "Dendritic cell-derived exosomes could be considered as novel peptide-based vaccines because exosomes harbor a discrete set of proteins, bear functional MHC class I and II molecules that can be loaded with synthetic peptides of choice, and are stable reagents that were safely used in pioneering phase I studies". Because of their ability to induce immune responses, EVs are a good vaccine candidate for alphavirus vaccines, either independently or for use in conjunction with vaccine platforms that are currently in development.

Described herein is the characterization of immune responses induced by the EVs in a murine model and evaluation of protection from an aerosol challenge of infectious VEEV.

Results.

HIV-1 infections of T-cells were used to demonstrate the isolation and characterization of EVs. Additionally, the data suggested that viral glycoproteins were included in the EVs and were detected using proteomic approaches.

EVs from HIV-1 Infected Culture Supernatants have Virus-Derived microRNA.

HIV produces many small noncoding RNA species of which the viral trans-activation response (TAR) element RNA is the most predominant. TAR RNA can be readily detected in serum samples obtained from HIV-positive patients and in culture supernatants of infected cells. To determine if EVs obtained from HIV-1 infected cells contained the HIV-derived TAR RNA, EVs were enriched from culture supernatants, validated them by western blots for marker proteins and confirmed the presence of TAR RNA by quantitative RT-PCR. Determined were the levels of all the other viral RNAs in the enriched fraction and observed that TAR RNA was in vast excess over all the other viral RNAs, thus ruling out contamination by virus particles.

EVs from Infected Culture Supernatants Contain Viral Proteins.

Detailed proteomic profiles of EVs from acutely infected cells were obtained by unbiased (mass spectrometry [MS]) proteomic methods. 110 host proteins were observed that were incorporated in the EVs in an infection-dependent manner (data not shown), and many viral proteins (Table 1).

TABLE 1

Viral proteins incorporated into EVs derived from virus-infected cells.

| Reference | P(pro) | Score(Xc) | M. Wt | Accession # |
|---|---|---|---|---|
| Capsid | 9.99E−16 | 20.24 | 25563.0 | 19172948 |
| Pr55 (Gag) | 6.99E−15 | 130.26 | 55894.4 | 9629360 |
| Gag-Pol | 3.01E−13 | 40.21 | 161939.3 | 28872819 |
| p6 | 1.83E−10 | 10.23 | 5780.9 | 19172951 |
| Reverse Transcriptase | 2.23E−10 | 10.13 | 64439.1 | 25121907 |
| p2 | 7.37E−09 | 10.13 | 1452.7 | 19172950 |
| Envelop surface protein, gp160, precursor | 9.67E−09 | 20.16 | 97150.9 | 9629363 |

EVs can be Engineered to Express Cytoplasmic Proteins on Membranes.

Dr. Gould's laboratory has demonstrated that by tethering specific anchors onto proteins, cytoplasmic proteins can be targeted to membranes and secreted as a part of EVs. One such signal peptide that can be added on to the N-termini of the structural proteins encoded by the VEEV structural protein plasmid construct is an acylation tag. Their studies have revealed that a cytoplasmic protein TyA tagged with the acyl tag targeted the protein to vesicles efficiently where it colocalized with the membrane protein CD63 (a classical vesicular marker).

In summary, EVs enriched from culture supernatants of virus-infected cells contained viral noncoding RNA, viral proteins and host inflammatory mediators. EVs derived from virus-infected cells make naïve cells more susceptible to subsequent virus infection. Collectively, EVs are potent mediators of extracellular information transfer that is likely to have profound influences on infection spread and disease pathology.

Further methods comprise isolation and characterization (proteomic, inflammatory and transcriptomic profiles) of EVs isolated from VEEV-infected cells. And functional characterization of EVs includes the induction of phospho-signaling cascades, permeability and viral-susceptibility of target cells (endothelial cells).

Isolation and Characterization.

Cells of neuronal origin will be infected with TrD and TC-83 strains of VEEV. EVs will be isolated by a combination of filtration (0.22 µM filters), differential ultracentrifugation and gradient fractionation. The proteome of EVs derived from VEEV-infected cells will be determined by unbiased (mass spectrometry [MS]) and biased (reverse phase protein microarray [RPMA]) approaches. The data output will be bioinformatically analyzed to arrive at detailed profiles of protein components specific to virulent and attenuated infections. The inflammasome of EVs derived from VEEV-infected cells will be determined by a combination of ELISA and cytokine arrays. Transcriptome profiles of EVs from VEEV-infected cells will be determined by a combination of microarray profiling and RNAseq.

In order to determine how EVs originating from VEEV-infected neuronal cells modulate the host phospho-signaling environment that contributes to endothelial cell damage, endothelial cells will be exposed to EVs and analyze changes in phospho-protein profiles by MS and RPMA. Changes in permeability of target cells will be evaluated by in vitro permeability assays that evaluate FITC-Dextran mobilization. Susceptibility of naïve endothelial cells to VEEV infection due to prior exposure to EVs will be evaluated by incubating naïve cells with EVs after which the "conditioned" cells will be exposed to TrD or TC-83 virus. Viral multiplication in the target cells will be determined by a combination of qRT-PCR and plaque assays.

The proteomic and transcriptomic profile of EVs that arise from VEEV infected cells will be compiled. These studies will be carried out simultaneously with virulent and infected strains; the information will directly correlate with viral virulence. Information about the functional roles of EVs in affecting barrier function and potentiating infection susceptibility of endothelial cells will be assessed.

Disclosed methods can comprise a) isolation, characterization of EVs originating from TC-83 and TrD infected neuronal cells; b) proteomic and transcriptomic characterization of EVs from infected neuronal cells; c) functional characterization of EVs: inflammatory and phospho-proteomic effects in target endothelial cells after exposure to EVs originating from VEEV infected cells; d) functional characterization of EVs: changes in endothelial permeability; changes in susceptibility to subsequent viral infection after EV exposure.

Similar studies will be carried out for Eastern Equine Encephalitis Virus (EEEV) infection. Proteomic and transcriptomic signatures will be analyzed (and compared with our VEEV-EV study) to arrive at profiles that are specific to EEEV. The studies will include detailed EV characterization, MS and RPMA based proteome profiling, transcriptome profiling and functional assays. In terms of the viral proteome in EVs, we are particularly interested in determining whether the capsid and envelope proteins (E1, E2 and E3 and the 6K protein) are included in the EVs. If they are, they would pave the way for increased target susceptibility to virus by providing membrane attachment epitopes for facilitated virus entry.

Similar studies will be carried out for Western Equine Encephalitis Virus (WEEV) infection. In the case of WEEV infections, the main object of interest is to determine how EVs arising from infected cells contribute to the strain specific lethalities. Based on the time to death, eight strains of virulent WEEV could be classified into two pathotypes: a high-virulence pathotype, consisting of strains California, Fleming and McMillan, and a low-virulence pathotype, comprising strains CBA87, Mn548, B11, Mn520 and 71V-1658. The changes in virulence have been attributed to protein diversity in the different strains. The specific identities of individual proteins that correlate with altered virulence is unknown and this information will be critical to better understanding WEEV biology and development of novel vaccine candidates.

Figure 11:
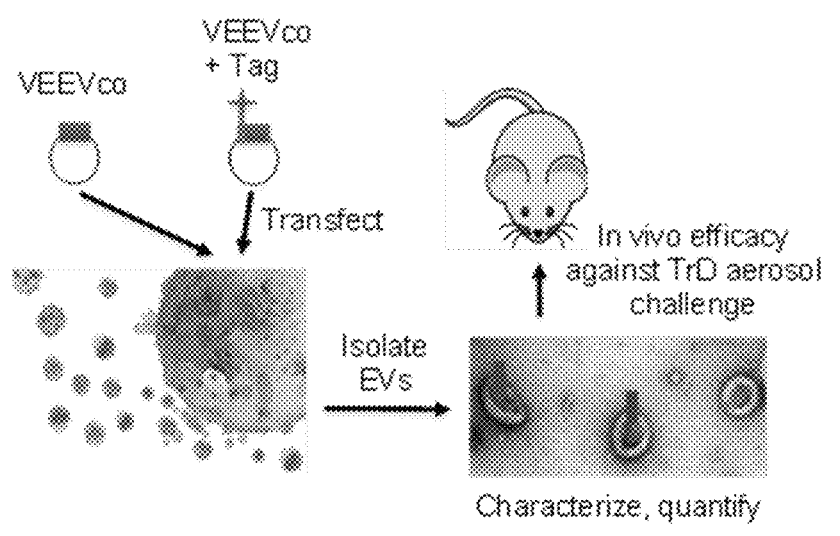

Disclosed are methods to engineer extracellular vesicles (EVs) to express VEEV structural proteins E1, E2, using the VEEVco plasmid as the driver (FIG. 11). The plasmid will be transfected into a variety of host cell lines and EV production will be characterized to evaluate the ability of engineered EVs to elicit a protective response in a mouse model following aerosol exposure to the virulent TrD strain of VEEV.

Transfection of VEEVco plasmid into a variety of host cell lines, isolate EVs from supernatants and determine expression of VEEV structural proteins on membrane surfaces is disclosed. Simultaneously, the VEEVco plasmid will be engineered to generate tagged versions of the viral structural proteins that will permit their incorporation into EVs if such an event does not happen with untagged proteins (VEEVco in its native state). It is hypothesized that even if the untagged proteins are released into EVs, tagging them with membrane-incorporation tags will confirm membrane expression, and may also aid in better incorporation into EVs. The efficacy of candidate EVs that express the target viral proteins in conferring protection to animals (mouse models) that are exposed to the TrD strain of VEEV by the aerosol route will be tested. The use of the EVs in conjunction with the parent VEEVco DNA vaccine candidate in a combinatorial capacity will be explored.

EVs have been demonstrated to be inducers of host innate immune responses and are therefore novel candidates that can be utilized as vaccines. As they are engineered to express viral structural proteins based on the parent VEEVco vector that has already demonstrated utility in conferring protection in a non-human primate model, they offer an opportunity for combinatorial vaccination regiments (prime boost approach).

Disclosed are methods: 1) to obtain a pool of engineered EVs that show robust expression of viral proteins on the surface; 2) to obtain a detailed profile of all the other components of the EVs to ensure specificity of the host immune response downstream following administration into animals; 3) to obtain detailed toxicity and efficacy profiles of EVs in a murine aerosol challenge model. Disclosed methods and compositions may comprise steps to: engineer EVs to express VEEV E1, E2 proteins from the VEEVco plasmid backbone; characterize compositions of EVs derived from host cells to map out host protein composition; and evaluate in vivo toxicity and efficacy of EVs in conferring protection to a mouse model organism following aerosol challenge.

Example 2: Extracellular Vesicles as Mediators of Pathogenic Responses in Venezuelan Equine Encephalitis Virus Infection Introduction.

Consequences of viral infections are often analyzed in a contained intracellular capacity to understand the interactions between the host and the pathogen and to connect these interactions to the pathology associated with the disease. While this approach provides a plethora of valuable information, it cannot be ignored that viral infections often result in pathologies in distant tissues far removed from the actual site of infection. It is striking to note that these off-target phenotypes (especially in case of systemic infections) are often so profound that alternative mechanisms (in addition to viral replication) come into play. Case in point, even though the brain is considered to be the most obvious and immediate target of viral infection and inflammatory responses in the case of alphavirus infections, the effects of the infection are felt in distant tissues including the liver, lungs etc. Hemorrhage and edema ensue indicative of barrier breach.

Background and Significance.

Venezuelan Equine Encephalitis Virus (VEEV) is known to infect dendritic cells and macrophages in lymphoid tissues that ultimately lead to neuroinvasion. The emphasis for the infectious route taken by the virus is the ability of the virus to capitalize on the migratory properties of the initial target cells. Therefore, intercellular communication and transport are key players in the systemic pathology associated with VEEV infections. High viremia is associated with viral spread to distal regions including endothelial tissues such as liver, spleen, lungs etc. Gross findings in fatal human cases include edema in the brain and infiltrations in lymph nodes, spleen, gastrointestinal tract, liver and lungs. Vasculitis and perivascular hemorrhage were also evident. Moderate to severe, interstitial pneumonia with infiltration of alveolar septa by neutrophils, lymphocytes, and macrophages was observed in the lungs. In the liver, hepatocellular degeneration and necrosis and inflammatory infiltrates were observed. Therefore, it is evident that VEEV infection leads to systemic phenotypes that are potent enough to involve multiple transmission mechanisms that exceed viral replication.

Extracellular vesicles (EVs) are nano- and micro-sized vesicles that are produced by all cell types and have been implicated extensively as vehicles of intercellular communication and information transfer between proximal and distal cells (1-3). The world of cancer research has recognized the critical role played by EVs in the mediation of disease associated phenotypes in distal tissues including cell migration, metastasis, angiogenesis and proteolysis. Effects of inflammatory mediators contained in EVs arising from

*Mycobacterium tuberculosis* infected cells have been described by the Schorey laboratory (4, 5). Additional evidence exists in the literature that implicates EVs as carriers of host inflammatory mediators and vascular modulators that lead to endothelial damage and barrier breach (6, 7).

The role of EVs in explosive and intense infections such as alphavirus infections requires investigation. Specifically, the exact role played by EVs arising from infected cells in distal tissues that lead to breach of endothelial barriers and the inflammatory consequences in the context of VEEV infection will be important to the development of novel, non-invasive diagnostic biomarkers and therapeutics.

The roles played by EVs arising from infected cells with regard to barrier damage have far reaching consequences that transcend alphavirus infections. As this is a phenotype that is commonly observed with many other pathogens such as bunyaviruses, filoviruses and flaviviruses, this study will provide functional basis for novel diagnostics and therapeutics to other infections as well.

Results.

HIV-1 infections of T-cells were utilized to demonstrate the significances of EVs to disease pathology and viral infection. EVs from acutely infected and latently infected cultured cells, primary cells and clinical samples were isolated and evaluated. Detailed proteomic profiles of EVs from acutely infected cells by unbiased (mass spectrometry [MS]) and phospho-signaling biased (reverse phase protein microarrays [RPMA]) proteomic approaches. Incorporation of host microRNA machinery components in EVs arising from HIV-infected cells has been evaluated.

Demonstrated herein were the incorporation of viral small RNAs, microRNAs and proteins in EVs and have obtained evidence for the mechanism to be a deliberate (instead of a random) process.

The data suggest that viral components incorporated into EVs are functional and modulate cell cycle progression of naïve target cells. EVs originating from infected cells made naïve cells more susceptible to viral infection and this may relate to increased expression of receptors on the surface. Modulation of target cell susceptibility may be regulated by both viral and host components incorporated into EVs. Preliminary analysis of inflammatory mediators (e.g., cytokines) in EVs demonstrate distinctive inclusion of specific cytokines in EVs originating from infected cells.

Data from clinical samples show that a combination of viral small RNA and host protein components in circulating EVs may be biomarkers indicative of disease progression in the host. The data suggest that inhibitors of exosome biogenesis inhibit viral spread to distal tissues in animal models of HIV-infections.

The experiments carried out will achieve the following: isolation, validation and characterization (proteomic, inflammatory and transcriptomic profiles) of EVs isolated from virulent (TrD) and attenuated (TC-83) VEEV infected cells; and functional characterization of EVs with regard to induction of inflammatory gene expression, apoptosis, phospho-signaling cascades, permeability and viral-susceptibility of target cells (endothelial cells).

Isolation and Validation of EVs:

Cells of neuronal origin will be infected with TrD and TC-83 strains of VEEV. All infected cells will be maintained in EV-free media to ensure that isolated EVs strictly originate from the infected cells (and not from EVs already present in culture media). EVs will be isolated by a combination of filtration (0.22 uM filters), differential ultracentrifugation and gradient fractionation methods. EVs will be validated and quantified by a combination of western blots for marker proteins (CD63, Alix, Hsp70, Tsg101, Hsp90, actin), protein quantitation and electron microscopy (EM restricted to TC-83 derived EVs).

Characterization of EV Proteome:

The proteome of EVs derived from TrD and TC-83 infected cells will be determined by both unbiased (mass spectrometry) and biased (reverse phase protein microarray and column chromatography) approaches. The data output will be bioinformatically analyzed to arrive at detailed interactive profiles of protein components specific to virulent and attenuated infections.

Characterization of EV Inflammasome:

The inflammasomes of EVs derived from TrD and TC-83 infected cells will be determined by a combination of ELISA, mass spectrometry and human cytokine membrane arrays.

Characterization of EV Transcriptome:

Transcriptome profiles of EVs from TrD and TC-83 infected cells will be determined by a combination of microarray profiling and RNAseq.

Functional Characterization of EVs:

In order to determine how EVs originating from VEEV infected neuronal cells contribute to endothelial cell damage, we will incubate EVs with endothelial cells for varying periods of time.

Total RNA isolated from the target cells will be analyzed for inflammatory gene expression by cytokine gene expression arrays. All data obtained from the arrays will be validated by individual qRT-PCR with gene specific primers. Corresponding protein expression will be evaluated by ELISA and western blots to correlate alterations in gene expression with protein expression.

Total protein isolated from the target cells will be analyzed by MS and RPMA approaches for changes in the phospho-proteome of the target cell. These two approaches will determine both signaling events that contribute to apoptosis and modulation of typical marker proteins associated with apoptosis (such as caspases). All data obtained from both events will be validated by targeted western blots.

Changes in permeability of target cells will be evaluated by in vitro permeability assays that evaluate FITC-Dextran mobilization (as measured by fluorescence values) in the presence of EVs from VEEV-infected cells. Positive controls such as IL-1β will be used to arrive at quantitative measures of permeability changes.

Susceptibility of naïve endothelial cells to VEEV infection due to prior exposure to EVs will be evaluated by incubating naïve cells with EVs after which the "conditioned" cells will be exposed to TrD or TC-83 virus. Viral multiplication in the target cells will be determined by a combination of qRT-PCR with virus specific primers or plaque assays.

Provided herein is a well-rounded proteomic and transcriptomic profile of EVs that arise from VEEV infected cells. As these studies will be carried out simultaneously with virulent and infected strains, the proteomic and transcriptomic information will directly correlate with viral virulence, spread and disease-phenotype associated with a virulent infection (which can be directly applied to the development of novel diagnostic biomarkers and therapeutics). Obtained will be information about the functional roles of EVs in affecting barrier function and potentiating infection susceptibility of endothelial cells in distant tissues away from the actual site of infection. The results will demonstrate the roles of EVs and the importance of extracellular information transfer in pathogenesis associated with alphavirus infections.

Methods and compositions disclosed include isolation, characterization of EVs originating from TC-83 and TrD infected neuronal cells; proteomic and transcriptomic characterization of EVs from infected neuronal cells; functional characterization of EVs—inflammatory and phospho-proteomic effects in target endothelial cells after exposure to EVs originating from VEEV infected cells; functional characterization of EVs including changes in endothelial permeability; changes in susceptibility to subsequent viral infection after exposure to EVs originating from VEEV infected cells.

Similar studies can be carried out in the context of Eastern Equine Encephalitis Virus (EEEV) infection and the observed changes compared to VEEV infection. EEEV is a far less studied virus than VEEV with more devastating consequences. Extensive neurological symptoms associated with edema and barrier breach are commonly observed in human cases long after the afflicted people have overcome the disease. Studies that focus on EVs and their contribution to EEEV associated pathology will provide critical biomarkers (that are a combination of viral, human proteins and transcriptome) that can permit early detection even when patients are in the flu-like symptoms stage.

Methods comprise infections of human cells with the virulent strain of EEEV and isolate EVs at various time points of infection. Analysis will be carried out for proteomic and transcriptomic signatures that will be compared with the results from the VEEV study to arrive at profiles that are specific to EEEV. The studies will include detailed EV characterization, MS and RPMA based proteome profiling, RNA seq and transcriptome profiling and functional assays.

In terms of the viral proteome in EVs, methods may comprise determining whether capsid and envelop proteins including E1, E2 and E3 and the 6K protein are included in the EVs. If they are, they would easily pave the way for increased target susceptibility to virus by providing membrane attachment epitopes for facilitated virus entry. This can be experimentally evaluated in the system where protein inclusion, mRNA inclusion in vesicles and their expression, membrane targeting in target cells can be determined.

Similar studies can be carried out in the context of Western Equine Encephalitis Virus infection. In the case of WEEV infections, the main object of interest is to determine how EVs arising from infected cells contribute to the strain specific lethalities that are associated with WEEV. Based on the time to death, eight strains of virulent WEEV can be classified into two pathotypes: a high-virulence pathotype, consisting of strains California, Fleming and McMillan, and a low-virulence pathotype, comprising strains CBA87, Mn548, B11, Mn520 and 71V-1658. The changes in virulence have been attributed to protein diversity in the different strains. The specific identities of individual proteins that correlate with altered virulence is unknown and this information will lead to a better understanding of WEEV biology and the development of novel vaccine candidates.

The ultimate outcome from the studies described herein will be a prototypical study of a fundamental host mechanism that drives the virulence phenotypes associated with alphavirus infections. EVs and intercellular communication have been extensively implicated in multiple disease states and are likely candidates that can facilitate systemic viral spread in explosive infections such as alphaviral infections.

Example 3: Engineered EVs Purified by Ultracentrifugation Methods

Figure 7:
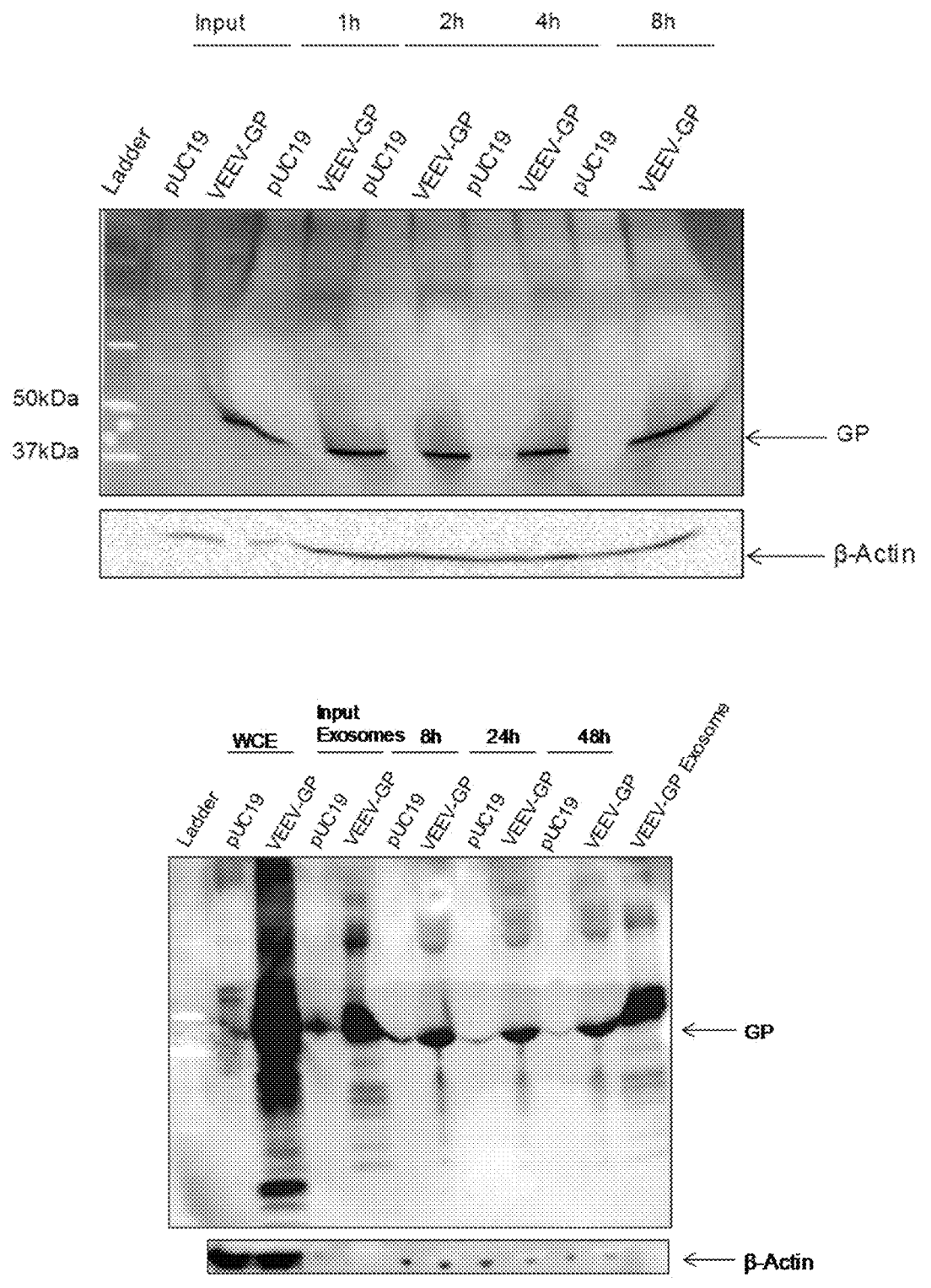

A DNA plasmid that encoded the glycoprotein E2 of Venezuelan Equine Encephalitis Virus (VEEV) was transfected into human 293Tcells cultured in the presence of exosome free media. Supernatants from transfected cells were collected at 24 and 48 hours post transfection and subjected to a low speed centrifugation @10,000 rpm for 10 minutes. The supernatant was transferred to a plastic container that can be safely used for high speed centrifugation. The supernatant was subjected to two rounds of high speed centrifugation at 100,000 rpm (for one hour each). The supernatant after the two rounds was discarded and the pellet, which contains the extracellular vesicle population, was resuspended in phosphate buffered saline (PBS), and stored at 4° C. The vesicle suspension was quantified using total protein quantification by the Bradford method and verified for protein content by resolution on a polyacrylamide gel by electrophoresis. The vesicle identity was validated by performing western blots with antibodies to known vesicle components including CD63, Alix and Hsp70. Finally, the presence of VEEV glycoprotein in the vesicles was confirmed by western blotting using antibodies against the VEEV E2 glycoprotein. The results are shown in FIG. 5 and FIG. 6A-D. The foreign protein entity that is enclosed in the EVs are protected from degradation and can be detected in EV preparations stored at room temperature for up to 48 hours (FIG. 7). This result provides an advantage to enclosing the deliverable protein into the vesicle platform to increase stability of the antigen and to partially or completely eliminate cold chain for transport and storage purposes.

Figures 8A, 8B:
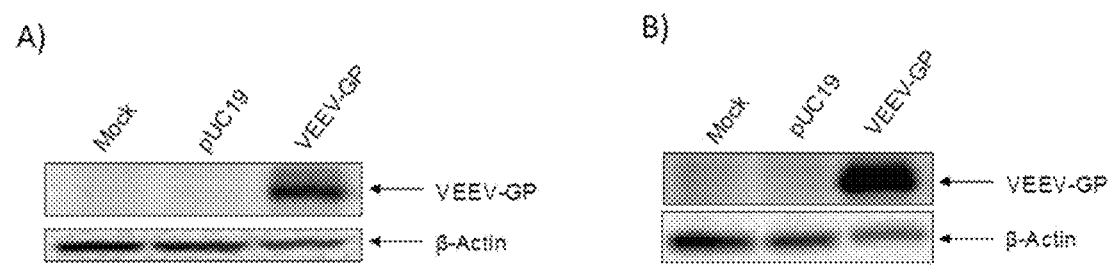

The foreign protein entity can be detected one or more types of recipient cells. For example, the foreign protein entity can be detected when the recipient cell was overlaid with the purified EVs as shown in FIGS. 8A-B. This demonstrates that the foreign protein can be introduced into immune active cells, such as macrophages (see FIG. 8B, in a THP-1 macrophage cell line).

Example 4: Schematic of the Process of Producing Extracellular Vesicles

A schematic representation of the process of generating extracellular vesicles (EVs) using adherent cells that may be harvested for therapeutic application is shown in FIG. 3. Illustrated is the front end of processing where vectors such as those shown in FIG. 1 can be transfected into recipient cells. The nucleic acid constructs described herein may have clinical utility. For example, the vectors (for example, see the pEV-vector in FIG. 1) can be transfected into FDA approved cell lines (e.g., HEK293 cells). These vectors may provide for selection in a restrictive growth medium, and successive passages may result in the establishment of a permanent cell line that expresses the antigen sequence(s) of interest. Said cell lines can then be cultured as biofactories, and supernatants from these cells can be harvested periodically. Such supernatants will be rich in secreted vesicular material which may be concentrated by multiple methodologies including, for example, ultracentrifugation or bead/antibody based concentration methods. These enriched extracellular vesicles may then be further purified using specific marker based concentration approaches including for example, FACS sorting which can yield homogenous populations of extracellular vesicles. Such second level enrichment may be achieved via receptor specific protein markers as included in the vector design described herein.

Example 5: Incorporation of Viral Glycoprotein (VEEV-GP)

To demonstrate that a target antigen of interest, the viral glycoprotein (VEEV-GP), is a part of the early organization in a cell that will eventually result in secretion along with marker proteins that are indigenous to secreted extracellular vesicles, colocalization studies were carried out using HEK293T cells that were transfected with a plasmid construct that expressed the viral glycoprotein (red signal in FIG. 4; VEEV-GP). Transfected cells were fixed and localization of VEEV-glycoprotein and CD63 were determined by using antibodies that were specific to the two proteins. Secondary antibody staining resulted in a green signal for CD63 and a red signal for VEEV-GP (see FIG. 4). Merging of the two images produced a yellow to orange signal demonstrating sufficient enough overlap of the green and red images (FIG. 4, merge). These results demonstrate that the VEEV-glycoprotein is capable of colocalizing in extracellular vesicles along with other secreted marker proteins.

REFERENCES

1. Meckes D G Jr, Raab-Traub N. Microvesicles and viral infection. J Virol. 2011 December; 85(24):12844-54.
2. Pegtel D M, Cosmopoulos K, Thorley-Lawson D A, van Eijndhoven M A, Hopmans E S, Lindenberg J L, de Gruijl T D, WUrdinger T, Middeldorp J M. Functional delivery of viral miRNAs via exosomes. Proc Natl Acad Sci USA. 2010 Apr. 6; 107(14):6328-33.
3. Pegtel D M, van de Garde M D, Middeldorp J M. Viral miRNAs exploiting the endosomal-exosomal pathway for intercellular cross-talk and immune evasion. Biochim Biophys Acta. 2011 November-December; 1809(11-12): 715-21.
4. Singh P P, LeMaire C, Tan J C, Zeng E, Schorey J S. Exosomes released from *M. tuberculosis* infected cells can suppress IFN-γ mediated activation of naïve macrophages. PLoS One. 2011 Apr. 14; 6(4):e18564.
5. Giri P K, Kruh N A, Dobos K M, Schorey J S. Proteomic analysis identifies highly antigenic proteins in exosomes from *M. tuberculosis*-infected and culture filtrate protein-treated macrophages. Proteomics. 2010 September; 10(17): 3190-202.
6. Morel O, Toti F, Hugel B, Freyssinet J M Cellular microparticles: a disseminated storage pool of bioactive vascular effectors. Curr Opin Hematol. 2004 May; 11(3): 156-64.
7. Liu M L, Scalia R, Mehta J L, Williams K J. Cholesterol-induced membrane microvesicles as novel carriers of damage-associated molecular patterns: mechanisms of formation, action, and detoxification. Arterioscler Thromb Vasc Biol. 2012 September; 32(9):2113-21.

What is claimed is:

1. A single nucleic acid construct comprising a vector, wherein the vector comprises:
   a) a first nucleic acid sequence, wherein the first nucleic acid sequence comprises one or more antigenic sequences of interest, one or more spacer sequences and one or more hydrophobic anchor sequences, wherein the first nucleic acid sequence is operably linked to a first transcriptional control element;
   b) a second nucleic acid sequence, wherein the second nucleic acid sequence encodes one or more pathogen-associated molecular pattern (PAMP) sequences, wherein the second nucleic acid sequence is operably linked to a second transcriptional control element; and wherein the PAMP sequence is a bacterial flagellin, lipoteichoic acid from a gram-positive bacteria, a peptidoglycan, a double-stranded RNA or fragment thereof, or a secreted viral protein;
   c) a third nucleic acid sequence, wherein the third nucleic acid sequence encodes one or more cell surface receptor binding sequences, wherein the third nucleic acid sequence is operably linked to a third transcriptional control element; and
   d) a selectable marker.

2. The single nucleic acid construct of claim 1, wherein the vector is a viral vector.

3. The nucleic acid construct of claim 1, wherein the first transcriptional control element is a promoter selected from the group consisting of SV40, CMV, SP6, T7, GAL4, Lac, polyhedron and tet.

4. The nucleic acid construct of claim 1, wherein the second transcriptional control element is a promoter selected from the group consisting of SV40, CMV, SP6, T7, GAL4, Lac, polyhedron and tet.

5. The nucleic acid construct of claim 1, wherein the third transcriptional control element is a promoter selected from the group consisting of SV40, CMV, SP6, T7, GAL4, Lac, polyhedron and tet.

6. The nucleic acid construct of claim 1, wherein the one or more antigenic sequences of interest encodes one or more peptides derived from a virus, a toxin, a bacterium or an allergen; and wherein the one or more antigenic sequences of interest are separated by a spacer sequence or is contiguous, or is contiguous with the one or more hydrophobic anchor sequences.

7. The nucleic acid construct of claim 6, wherein the one or more peptides is derived from a virus, a toxin, a bacterium or an allergen is a full sequence, a fragment sequence or a combination thereof.

8. The nucleic acid construct vector of claim 1, wherein the one or more hydrophobic anchor sequences comprises a nucleic acid sequence capable of encoding one or more ubiquitin proteins.

9. The nucleic acid construct of claim 6, wherein the virus is a retrovirus, togaviridae, flaviviridae, arenaviridae, orthomyxovirus, rhabdovirus, reovirus, picornavirus, herpes, adenovirus or poxvirus.

10. The nucleic acid construct of claim 6, wherein the toxin is *Bordetella pertussis* adenylate cyclase toxin, hemolysins, leukotoxins, *E. coli* containing toxin, a jellyfish toxin, snake toxin or a honeybee toxin.

11. The nucleic acid construct of claim 6, wherein the allergen is a venom.

12. The nucleic acid construct of claim 1, wherein the one or more PAMP sequences are separated by a spacer sequence or is contiguous.

13. The nucleic acid construct of claim 1, wherein expression of the one or more cell surface receptor binding sequences is regulatable.

14. The nucleic acid construct of claim 1, wherein the one or more cell surface receptor binding sequences is capable of encoding one or more cell surface receptor binding peptides.

15. The nucleic acid construct of claim 1, wherein the selectable marker is an antibiotic resistance gene.

16. A composition comprising the single nucleic acid construct of claim 1 and a pharmaceutical carrier.

17. A method of treating a subject at risk for or having an infectious disease, the method comprising administering to the subject an effective amount of a pharmaceutical composition comprising the nucleic acid construct of claim 1.

18. A method of making an extracellular vesicle, the method comprising:
   a) Introducing a first nucleic acid sequence, wherein the first nucleic acid sequence comprises one or more antigenic sequences of interest, one or more spacer sequences and one or more hydrophobic anchor sequences, operably linked to a first transcriptional control element;
   b) introducing a second nucleic acid sequence, wherein the second nucleic acid sequence comprises one or more pathogen-associated molecular pattern sequences operably linked to a second transcriptional control element;
   c) introducing a third nucleic acid sequence, wherein the third nucleic acid sequence comprises one or more cell surface receptor binding sequences operably linked to a third transcriptional control element; and
   d) maintaining the cell under conditions that allow expression of a), b), and c) of the extracellular vesicle;
   wherein the one or more antigenic sequences of interest is a nucleic acid sequence encoding one or more peptides derived from a virus, a toxin, a bacterium or an allergen.

\* \* \* \* \*